(12) United States Patent
Nishida et al.

(10) Patent No.: US 6,465,618 B1
(45) Date of Patent: Oct. 15, 2002

(54) MITOGEN ACTIVATED PROTEIN KINASE (MAPK) KINASE

(75) Inventors: Eisuke Nishida; Tetsuo Moriguchi, both of Kyoto; Osamu Matsuzaki, Fuji, all of (JP)

(73) Assignee: Asahi Kasei Kabushikiki Kaisha, Osaka (JP)

( * ) Notice: Subject to any disclaimer, the term of this patent is extended or adjusted under 35 U.S.C. 154(b) by 0 days.

(21) Appl. No.: 09/446,754
(22) PCT Filed: Jul. 3, 1998
(86) PCT No.: PCT/JP98/03016
§ 371 (c)(1), (2), (4) Date: Dec. 27, 1999
(87) PCT Pub. No.: WO99/01559
PCT Pub. Date: Jan. 14, 1999

(30) Foreign Application Priority Data

Jul. 3, 1997 (JP) .............................................. 9-193207

(51) Int. Cl.$^7$ .......................... C07K 14/47; C12N 5/10; C12N 15/52; C12N 15/63
(52) U.S. Cl. ...................... 530/350; 536/23.2; 536/24.3; 536/24.31; 435/69.1; 435/71.1; 435/71.2; 435/194; 435/471; 435/320.1; 435/325; 435/252.3; 435/254.11
(58) Field of Search .......................... 530/350; 536/234, 536/23.2, 243, 24.31; 435/71.1, 71.2, 471, 325, 320.1, 252.3, 254.11, 69.1, 194

(56) References Cited

U.S. PATENT DOCUMENTS 6,136,596 A 10/2000 Davis et al.

OTHER PUBLICATIONS

Mikayama et al. Proc. Natl. Acad. Sci. USA vol. 90, pp. 10056–10060., 1993.*
Voet et al. Biochemistry. John Wiley & Sons, Inc., pp. 126–128 and 228–234, 1990.*
Foltz et al., "Human Mitogen–activated Protein Kinase Kinase 7 (MKK7) Is a Highly Conserved c–Jun N–terminal Kinase/Stress–activated Protein Kinase (JNK/SAPK) Activated by Environmental Stresses and Physiological Stimuli", *The Journal of Biological Chemistry*, vol. 273, No. 15, pp. 9344–9351, 1998.
Glise et al., "hemipterous Encodes a Novel Drosophila MAP Kinase Kinase, Required for Epithelial Cell Sheet Movement", *Cell*, vol. 83, pp. 451–461, 1995.
Holland et al., "MKK7 Is A Stress–activated Mitogen–activated Protein Kinase Kinase Functionally Related to hemipterous", *The Journal of Biological Chemistry*, vol. 272, No. 40, pp. 24994–24998, 1997.
Lawler et al., "SKK4, a novel activator of stress–activated protein kinase–1 (SAPK1/JNK)", *FEBS Letters*, vol. 414, pp. 153–158, 1997.
Lin et al., "Identification of Dual Specificity Kinase That Activates the Jun Kinases and p38–Mpk2", *Science*, vol. 268, pp. 286–290, 1995.
Lu et al., "Identification of c–Jun NH$_2$–terminal Protein Kinase (JNK) –activating Kinase 2 as an Activator of JNK but Not p38", *The Journal of Biological Chemistry*, vol. 272, No. 40, pp. 24751–24754, 1997.
Moriguchi et al., "Evidence for Multiple Activators for Stress–activated Protein Kinases/c–Jun Amino–terminal Kinases", *The Journal of Biological Chemistry*, vol. 270, No. 22, pp. 12969–12972, 1995.
Moriguchi et al., "A novel SAPK/JNK kinase, MKK7, stimulated by TNFα and cellular stresses", *The EMBO Journal*, vol. 16, No. 23, pp. 7045–7053, 1997.
Tournier et al., "Mitogen–activated protein kinase kinase 7 is an activator of the c–Jun NH$_2$–terminal kinase", *Proc. Natl. Acad. Sci. USA*, vol. 94, pp. 7337–7342, 1997.
Tournier et al., "The MKK7 Gene Encodes a Group of c–Jun NH$_2$–Terminal Kinase Kinases", *Molecular and Cellular Biology*, vol. 19, No. 2, pp. 1569–1581, 1999.
Sanchez et al., "Role of SAPK/ERK kinase–1 in the stress–activated pathway regulating transcription factor c–Jun", *Nature*, vol. 372, pp. 794–798, 1994.
Wu et al., "Molecular Cloning and Characterization of Human JNKK2, a Novel Jun NH$_2$–Terminal Kinase–Specific Kinase", *Molecular and Cellular Biology*, vol. 17, No. 12, pp.7407–7416, 1997.
Yan et al., "Activation of stress–activated protein kinase by MEKK1 phosphorylation of its activator SEK1", *Nature*, vol. 372, pp. 798–800, 1994.
Yang et al., "Molecular cloning and characterization of a human protein kinase that specifically activates c–Jun N–terminal kinase", *Gene*, vol. 212, pp. 95–102, 1998.
Yao et al., Activation of Stress–activated Protein Ki–nase/c–Jun N–terminal Protein Kinases (SAPKs/JNKs) by a Novel Mitogen–activated Protein Kinase Kinase (MKK7), *The Journal of Biological Chemistry*, vol. 272, No. 51, pp. 32378–32383, 1997.

* cited by examiner

Primary Examiner—Prema Mertz
(74) Attorney, Agent, or Firm—Young & Thompson

(57) ABSTRACT

Disclosed is a substantially pure MAPK (mitogen-activated protein kinase) kinase derived from a vertebrate, which is activated by a stimulus induced by TNF-α and/or by a stimulation of Fas antigen, and which in turn activates SAPK/JNK, but does not activate p38; and also disclosed is a DNA coding for the same. By the use of the novel MAPK kinase and the DNA coding for the same of the present invention, it has become possible to screen a novel substance having the capability to treat or prevent diseases resulting from an excess activation or inhibition of a MAP kinase cascade, and also to provide a diagnostic reagent for such diseases. In addition, the DNA of the present invention encoding the MAPK kinase can be used as a gene source for gene therapy. Further disclosed are a replicable recombinant DNA which comprises a replicable expression vector and, operably inserted therein, the above-mentioned DNA; a cell of a microorganism or cell culture, which is transformed with the above-mentioned replicable recombinant DNA; a polypeptide of a dominant negative form of the above-mentioned MAPK kinase and a DNA coding for the same; and an antibody capable of binding specifically to the above-mentioned MAPK kinase.

7 Claims, 7 Drawing Sheets

Fig. 1

```
MKK7        MAASSLEQKLSRLEAKLKQENREARRRIDLNLDISPQRP--RP---IIVITLSPAPA
Hep         MSTIEFETIGSRLQSLEAKLQAQN-ESHDQIVLSGARGPVVSGSVPSARVPPLATSASAA
SEK1        MAAPSPSG------GGGSGGG---------GGTPGPIGP---P----ASGHPAVSSM

MKK7        PSQRAALQLPLANDGGS----------------RSPSSESSPQ---------------
Hep         TSATHAPSLGASSVSGSGISIAQRPAPPVPHATLRSPSASSSSSSRSAFRSAAPATGLRW
SEK1        Q----GKRKALKLNFAN----------------PPVKSTAR---------------

MKK7        ---HPTP------PTRPRHMLG----------LPSTLFTPRSMESIEIDQKLQEIMKQTG
Hep         TYTPPTTRVSRATPTLPMLSSGPGGDVECTRPVILPLPTPPHPPVSETDMKLKIIMEQTG
SEK1        -------------FTLNPNTTG---------------VQNP---HIERLRTHSIESSG

MKK7        YLTIGG-QRYQAEINDLENLGEMGSGTCGQVWKMRFRKTGHIIAVKQMRRSGNKEENKRI
Hep         KLNLNG-RQYPTDINDLKHLGDLGNGTSGNVVKMMHLSSNTIIAVKQMRRTGNAEENKRI
SEK1        KLKISPEQHWDFTAEDLKDLGEIGRGAYGSVNKMVHKPSGQIMAVKRIRSTVDEKEQKQL

MKK7        LMDLDVVLKSHDCPYIVQCFGTFITNTDVFIAMELMGTCAEKLKKRMQ----GPIPERIL
Hep         LMDLDVVLKSHDCKYIVKCLGCFVRDPDVWICMELMSMCFDKLLKLSK----KPVPEQIL
SEK1        LMDLDVVMRSSDCPYIVQFYGALFREGDCWICMELMSTSFDKFYKYVYSVLDDVIPEEIL

MKK7        GKMTVAIVKALYYLKEKHGVIHRDVKPSNILLDERGQIKLCDFGISGRLVDSKAKTRSAG
Hep         GKVTVATVNALSYLKDKHGVIHRDVKPSNILIDERGNIKLCDFGISGRLVDSKANTRSAG
SEK1        GKITLATVKALNHLKENLKIIHRDIKPSNILLDRSGNIKLCDFGISGQLVDSIAKTRDAG

MKK7        CAAYMAPERIDPPDPTKPDYDIRADVWSLGISLVELATGQFPYKNCKTDFEVLTKVLQEE
Hep         CAAYMAPERID---PKKPKYDIRADVWSLGITLVELATARSPYEGCNTDFEVLTKVLDSE
SEK1        CRPYMAPERIDP-SASRQGYDVRSDVWSLGITLYELATGRFPYPKWNSVFDQLTQVVKGD

MKK7        PPLLPGHMG--FSGDFQSFVKDCLTKDHRKRPKYNKLLEHSFIKHYEILEVDVASWFKDV
Hep         PPCLPYGEGYNFSQQFRDFVIKCLTKNHQDRPKYPELLAQPFIRIYESAKVDVPNWFQSI
SEK1        PPQLSNSEEREFSPSFINFVNLCLTKDESKRPKYKELLKHPFILMYEERTVEVACYVCKI

MKK7        MAKTESPRTSGVLSQHHLPFFSGSLEESPTSPPSPKSFPLSPAIPQAQAEWVSGR
Hep         KDND----------------CGQWRSN------------APEVT----------
SEK1        LDQMP----------------ATPSSP--------------MYVD----------
```

MITOGEN ACTIVATED PROTEIN KINASE (MAPK) KINASE

BACKGROUND OF THE INVENTION

1. Field of the Invention

The present invention relates to a novel MAPK kinase derived from a vertebrate and a DNA coding for the same. More particularly, the present invention is concerned with a MAPK kinase which is activated by a stimulus induced by TNF-α and/or by a stimulation of Fas antigen, and which in turn activates SAPK/JNK, but does not activate p38. Also, the present invention is concerned with a DNA coding for the above-mentioned MAPK kinase. By the use of the MAPK kinase and the DNA coding for the same, it has become possible to provide a method for screening a novel substance which can be used for treating or preventing diseases resulting from an excess activation or inhibition of a MAP kinase cascade, and also to provide a diagnostic reagent for such diseases. The present invention is also concerned with a replicable recombinant DNA which comprises a replicable expression vector and, operably inserted therein, the above-mentioned DNA; a cell of a microorganism or cell culture, which is transformed with the above-mentioned replicable recombinant DNA; a polypeptide of a dominant negative form of the above-mentioned MAPK kinase and a DNA coding for the same; and an antibody capable of binding specifically to the above-mentioned MAPK kinase.

2. Prior Art

MAP (mitogen-activated protein) kinase (MAPK) was first discovered in the late 1980's as a serine/threonine kinase (Ser/Thr kinase; i.e., an enzyme capable of phosphorylating serine or threonine residues in a protein) which is activated by stimuli, such as insulin {Sturgill, T. W. et al., Biochim. Biophys. Acta, 1092: 350–357 (1991)}, various cell growth factors and tumor promoters {Nishida, E. et al., Int. Rev. Cytol., 138: 211–238 (1992)}. Studies over the past 10 years revealed that the MAP kinase is a major functional unit of an intracellular signal transduction system which mediates cell determination and functional regulation of eukaryotic cells in response to extracellular stimuli {Nishida, E. et al., Trends Biochem. Sci., 18: 128–131 (1993); Marshall, C. J., Curr. Opin. Genet. Dev., 4: 82–89 (1994); and Cobb, M. H. et al., J. Biol. Chem., 270: 14843–14846 (1995)}. Particularly, an important achievement in the field of cell biology of the 1990's is an elucidation of a signal transduction pathway which starts from a cell growth factor receptor having tyrosine kinase activity, through an adapter molecule composed of SH2 (Src homology 2) and SH3 (Src homology 3), Ras (an oncogene product which is a GTP-binding protein) and Raf-1 (an oncogene product which is a serine/threonine kinase), and leading to the MAP kinase. The studies revealed that this signal transduction pathway is a central pathway responsible for determining cell proliferation, cell differentiation, and cell development of higher eukaryotic organisms.

A signal transduction molecule is converted into an activated form (switched "on") by a signal in the upstream of a signal transduction pathway, and the activated molecule returns to an inactive form (switched "off") after transducing the signal to the downstream thereof. The regulatory mechanism for switching on/off the MAP kinase has an interesting feature. That is, phosphorylation of T and Y in the TEY (Thr-Glu-Tyr in 3-letter abbreviation) sequence located in the boundary region between the kinase subdomains VII and VIII is required for activating the MAP kinase. An enzyme called MAPK kinase (MAPKK) or MAPK/ERK kinase (MEK) was identified as an enzyme which catalyzes the phosphorylation (that is, activation) of these amino acid residues. MAPK kinase is a dual specificity kinase which is capable of phosphorylating both serine/threonine residue and tyrosine residue.

For activating a MAPK kinase, it is necessary to phosphorylate two serine and/or threonine residues (i.e., two serine residues, two threonine residues, or one serine residue and one threonine residue) located in the boundary region between the kinase subdomains VII and VIII, and a serine/threonine kinase responsible for this phosphorylation is designated MAPKK kinase (MAPKKK). The above-mentioned Raf-1 is one example of MAPKK kinase, and the following cascade reaction:

Ras→Raf-1 (i.e., MAPKKK)→MAPKK→MAPK, is one of the major signal transduction pathways. The cascade reaction consisting of three kinase molecules,

MAPKKK→MAPKK→MAPK, is called a MAP kinase signal cascade.

The above-mentioned signal transduction system,

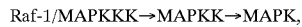

Raf-1/MAPKKK→MAPKK→MAPK, is the first identified MAP kinase signal cascade and, therefore, this system is frequently called "classical MAP kinase signal pathway". Later studies revealed the existence of various kinases which are similar to the classical MAP kinase. One example of such a kinase is stress-activated protein kinase (SAPK). This enzyme has been identified as a kinase which is activated in response to a stimulation of a cell by chemical stresses (such as protein synthesis inhibitor) or physical stresses (such as heat shock or change in osmotic pressure) {Kyriakis, J. M., Nature, 369: 156–160 (1994)}. SAPK was later found to be identical to c-Jun N-terminal kinase (JNK), which is a kinase identified independently from and contemporaneously with SAPK, and phosphorylates the N-terminus of transcription factor Jun to increase the transcription activity thereof {Derijard, B., Cell, 76: 1025–1037 (1994)} (hereinafter, SAPK and JNK are frequently referred to as "SAPK/JNK"). SAPK/JNK has homology to the classical MAP kinase, and a sequence corresponding to the TEY sequence necessary for the activation of the classical MAP kinase is TPY (Thr-Pro-Tyr) in SAPK/JNK. SAPK/JNK is similar to the classical MAP kinase in that the Thr and Tyr residues in the above-mentioned sequence are phosphorylated by a sole MAPK kinase in the upstream thereof, but the major activator of SAPK/JNK is a MAPK kinase called SAPK/ERK kinase-1 (SEK1) or mitogen-activated protein kinase kinase 4 (MKK4) (hereinafter, SEK1 and MKK4 are frequently referred to as "SEK1/MKK4") {Lin, A. et al., Science, 268: 286–290 (1995); Sanchez, I., Nature, 372: 794–798 (1994); and Moriguchi, T. et al., J. Biol. Chem., 270: 12969–12972 (1995)}. Therefore, with respect to the classical MAP kinase, the classical MAPK kinase functions as an activation factor in the upstream of the signal transduction pathway, and a novel MAP kinase is phosphorylated (activated) specifically by a different MAPK kinase. With respect to a MAPKK kinase in the upstream of a pathway leading to SAPK/JNK, a kinase called MEKK is known, but the existence of other kinases capable of functioning as a MAPKK kinase is not known.

In addition to SAPK/JNK mentioned above, a kinase similar to MAP kinase, which is simply called "p38" after its molecular weight, is also known in the art. This kinase has been identified and cloned as a protein which is tyrosine phosphorylated in an early stage after stimulating lymphocytes {Han, J. et al., Science, 265: 808–811 (1994)}. Contemporaneously with p38, a protein which binds to a cytokine-suppressive anti-inflammatory drug (CSAID; a drug for suppressing the production of anti-inflammatory cytokines in lymphocytes) has been independently identified and called CSAID binding protein (CSBP) {Lee, J. C. et al., Nature, 372: 739–746 (1994)}. At present, this protein is confirmed to be identical with p38. Further, MPK2, an independently isolated kinase which is activated by stress stimuli, is also found to be identical with p38 {Rouse, J. et al., Cell, 78: 1027–1037 (1994)} (Hereinafter, p38, CSBP and MPK2 are frequently referred to as "p38"). With respect to the above-mentioned TXY sequence (X is a predetermined amino acid residue) necessary for activating a MAP kinase, the amino acid residue "X" is "G" in p38, and p38 is activated as a result of the phosphorylation of the Thr and Tyr residues by a sole MAPK kinase in the upstream thereof. MKK3 and MKK6 are known as MAPK kinases which specifically activate p38 {Moriguchi, T. et al., J. Biol. Chem., 271: 26981–26988 (1996); and Cuenda, A. et al., EMBO J., 15: 4156–4164 (1996)}. The sequences of classical MAP kinase, SAPK/JNK and p38 are homologous to each other and, therefore, they constitute a superfamily. The MAPK kinases respectively specific for the above-mentioned three MAP kinases are also homologous to each other, and the MAPK kinases also constitute a superfamily in which MEK, SEK1/MKK4, MKK3, MKK6 and such are members thereof {Kyriakis, J. M. et al., J. Biol. Chem., 271: 24313–24316 (1996); and Davis, R. J., Trends Biochem. Sci., 19: 470–473 (1994)}. On the other hand, with respect to the MAPKK kinases located in the further upstream of the signal transduction pathway which are responsible for phosphorylating and activating each MAPK kinase, the homology among the MAPKK kinases is relatively low. For example, the homology among Raf, TAK1, MEKK, MLK3, Ask1 and Mos having the MAPKK kinase activity is only about 30% even within the kinase domains. This is in agreement with the role of the whole signal transduction system which is adapted to operate respective appropriate MAP kinase signal transduction pathways in response to a wide variety of stimuli.

SAPK/JNK and p38 are not activated by the growth factors which activate the classical MAP kinase, but they are activated by stresses, such as osmotic shock and heat shock, and cytokines, such as TNF-α (tumor necrosis factor-α or cachectin) and IL-1 (interleukin 1) {Kyriakis, J. M. et al., J. Biol. Chem., 271: 24313–24316 (1996); and Davis, R. J., Trends Biochem. Sci., 19: 470–473 (1994)}. Further, SAPK/JNK and p38 are activated under conditions at which cell death, such as UV radiation, and depletion of serum and/or growth factors are induced {Kyriakis, J. M. et al., J. Biol. Chem., 271: 24313–24316 (1996); and Davis, R. J., Trends Biochem. Sci., 19: 470–473 (1994)}. Unlike classical MAP kinase which is activated by a signal transmitted from a tyrosine kinase-type receptor, the characteristic feature of the signal transduction systems for SAPK/JNK and p38 is that these systems are initiated by various signals.

TNF-α mentioned above has various effects on inflammation, tissue disorder, immune response, and cell invasion into a focus, and these effects suggest the presence of a certain relationship between TNF-α and autoimmune diseases or graft-versus-host disease (GVHD) {J. Exp. Med., 166: 1280 (1987)}. Specifically, the role of TNF-α in the onset of inflammatory arthritis, such as rheumatoid arthritis, has been conceived {Lancet, 11: 244–247 (1989); and Ann. Rheumatic Dis. 51: 480–486 (1990)}. Administration of anti-TNF-α antibody to DBA/1 mouse either before or after the onset of arthritis relieves the inflammation accompanying collagenous arthritis, and it significantly lowers the degree of joint destruction {Williams, R. O. et al., Proc. Natl. Acad. Sci. USA, 89: 9784–9788 (1992)}. In addition, effectiveness of chimeric anti-TNF-α antibody for treating rheumatoid arthritis and Crohn's disease has been confirmed clinically {Derkx, B. et al., Lancet, 342: 173–174 (1993); Elliott, M. J. et al., Lancet, 344: 1105–1110 (1994); and Elliott, M. J. et al., Lancet, 344: 1125–1127 (1994)}.

Studies on the signal transduction mechanism of TNF-α is in a progress. Two types of receptors for TNF-α, namely, TNF-R1 having a molecular weight of 55 kD and TNF-R2 having a molecular weight of 75 kD are known in the art, and recently, molecules which associate with the TNF receptors have been directly cloned by using yeast two-hybrid system. Examples of cloned molecules which associate with TNF-R1 include TRADD (TNF-R1 associated death domain protein) {Hsu, H. et al., Cell, 81: 495–504 (1995)}, TRAP1, TRAP2 {Song, H. Y. et al., J. Biol. Chem., 270: 3574–3581 (1995)} and RIP {Stanger, B. Z. et al., Cell, 81: 513–523 (1995)}. Examples of cloned molecules which associate with TNF-R2 include TRAF1 and TRAF2 {Rothe, M. et al., Cell, 78: 681–692 (1994)}. While the molecules which associate with the TNF receptors are being identified, recent studies have revealed that NF-κB, ceramide kinase and MAP kinase are activated by TNF-α. It is reported that cell permeable derivatives of ceramide, such as C8-Cer (N-octanoylsphingocine) and C2-Cer (N-acetylsphingocine), exhibit a function similar to that of TNF-α {Kolesnick, R. et al., Cell, 77: 325–328 (1994)}, and these substances also activate the MAP kinase and the ceramide kinase. As apparent from the above, the knowledge on the signal transduction mechanism of TNF-α is making a rapid progress, but many problems remain unsolved. For example, the relationship between a receptor-associated protein (such as TRADD) and kinases in the mechanism for activating a signal transduction system, and a MAP kinase cascade activated by TNF-α are still unknown.

The above-mentioned SEK1/MKK4 is the only MAPK kinase that is known with respect to its function to phosphorylate SAPK/JNK. A stimulus induced by TNF-α will lead to the phosphorylation of SAPK/JNK, but this stimulus does not activate SEK1/MKK4. In this situation, the present inventors predicted the existence of an unidentified MAPK kinase which is activated by TNF-α and in turn, uses SAPK/JNK as a substrate and activates SAPK/JNK. Therefore, the goal of the present invention is to isolate a novel MAPK kinase gene and a protein encoded by the same which is activated by TNF-α and which phosphorylates SAPK/JNK, and to provide a method for using the novel gene and protein in the field of pharmaceutics and clinics.

SUMMARY OF THE INVENTION

The present inventors have made extensive and intensive studies with a view toward cloning a novel MAPK kinase. Particularly, the present inventors have successfully cloned a fragment of a novel MAPK kinase from the cDNA library of Xenopus oocyte, and have found that this fragment is similar to a MAPK kinase gene of Drosophila called hep. Subsequently, this novel MAPK kinase gene fragment was used as a probe to screen a mouse brain cDNA library, and a novel mouse MAPK kinase (hereinafter, frequently referred to as "MKK7") gene which is structurally belonging to the MAPK kinase family was cloned. Next, by using the nucleotide sequence of the novel mouse MAPK kinase, the present inventors have found candidates for human MKK7 among the clones registered in the EST (Expressed Sequence Tag) database. Based on the human EST sequences, the present inventors have successfully cloned the whole nucleotide sequence of human MKK7 from human heart mRNA. Unlike SEK1 and MKK6 which are the MAPK kinases known in the art, the above-mentioned mouse MKK7 specifically activates SAPK and does not activate p38 or SAPK3, and it has been confirmed that MKK7 is a MAPK kinase participating in the signal transduction pathway in vivo starting from TNF-α and leading to SAPK/JNK. In addition, the present inventors have also found the possibility for MKK7 to participate in the induction of apoptotic signals by Fas antigen. The present invention has been completed, based on these novel findings.

Therefore, it is a principal object of the present invention to provide a MAPK kinase, which is defined as a substantially pure MAPK kinase derived from a vertebrate, wherein the MAPK kinase has the following characteristics:

(a) the MAPK kinase is activated by a stimulus induced by TNF-α and/or by a stimulation of Fas antigen;

(b) the MAPK kinase activates SAPK/JNK; and (c) the MAPK kinase does not activate p38.

It is another object of the present invention to provide a DNA coding for the above-mentioned MAPK kinase.

It is another object of the present invention to provide a polypeptide which is a dominant negative form of the above-mentioned MAPK kinase, in which the polypeptide inhibits the activation of SAPK/JNK which is induced by TNF-α.

Still another object of the present invention is to provide a method for screening a substance having the capability to inhibit the activation of SAPK/JNK by the above-mentioned MAPK kinase.

The foregoing and other objects, features and advantages of the present invention will be apparent to those skilled in the art from the following detailed description and the appended claims taken in connection with the accompanying sequence listing and drawings.

BRIEF DESCRIPTION OF THE SEQUENCE LISTING

In the following sequences, the left end and right end of the nucleotide sequence are the 5' end and the 3' end, respectively; and the left end and right end of the amino acid sequence are the N-terminus and the C-terminus, respectively.

SEQ ID NO: 1 is the nucleotide sequence of MKK7 cDNA derived from human heart and the whole amino acid sequence encoded by the nucleotide sequence;

SEQ ID NO: 2 is the whole amino acid sequence of MKK7 derived from human heart;

SEQ ID NO: 3 is the nucleotide sequence of MKK7 cDNA derived from mouse brain and the whole amino acid sequence encoded by the nucleotide sequence;

SEQ ID NO: 4 is the whole amino acid sequence of MKK7 derived from mouse brain;

SEQ ID NO: 5 is the nucleotide sequence of a cDNA of an alternatively spliced form of MKK7 derived from mouse brain and the amino acid sequence encoded by the nucleotide sequence;

SEQ ID NO: 6 is the amino acid sequence of the alternatively spliced form of MKK7 derived from mouse brain;

SEQ ID NO: 7 is the nucleotide sequence of MKK7 cDNA fragment derived from Xenopus oocyte and the amino acid sequence encoded by the nucleotide sequence;

SEQ ID NO: 8 is the amino acid sequence of MKK7 fragment derived from Xenopus oocyte;

SEQ ID NO: 9 is the nucleotide sequence of a dominant negative form of MKK7 which was synthesized based on the nucleotide sequence of SEQ ID NO: 3, and the amino acid sequence encoded by the nucleotide sequence;

SEQ ID NO: 10 is the amino acid sequence of the synthesized dominant negative form of MKK7;

SEQ ID NO: 11 is the PCR primer used in 5' RACE method performed in Example 2 for amplifying the 5' end of human MKK7;

SEQ ID NO: 12 is the PCR primer used in 5' RACE method performed in Example 2 for amplifying the 5' end of human MKK7;

SEQ ID NO: 13 is the PCR primer used in 5' RACE method performed in Example 2 for amplifying the 5' end of human MKK7;

SEQ ID NO: 14 is the PCR primer used in 3' RACE method performed in Example 2 for amplifying the 3' end of human MKK7;

SEQ ID NO: 15 is the PCR primer used in 3' RACE method performed in Example 2 for amplifying the 3' end of human MKK7;

SEQ ID NO: 16 is the 5' end primer used in Example 2 for amplifying the sequence in-between the 5' and 3' sequences of human MKK7;

SEQ ID NO: 17 is the 3' end primer used in Example 2 for amplifying the sequence in-between the 5' and 3' sequences of human MKK7;

SEQ ID NO: 18 is the synthetic oligonucleotide used in Example 4 for preparing the dominant negative form of MKK7;

SEQ ID NO: 19 is the synthetic oligonucleotide used in Example 5 for preparing vector pSRα-HA1; and SEQ ID NO: 20 is the synthetic oligonucleotide used in Example 5 for preparing vector pSRα-HA1.

BRIEF DESCRIPTION OF THE DRAWINGS

In the accompanying drawings:

FIG. 1 shows an alignment of the amino acid sequence of mouse MKK7 with those of Drosophila Hep and mouse SEK1, and a bar (−) indicates the absence of a corresponding amino acid residue, and a shaded amino acid residue indicates the amino acid residue which is identical to that of MKK7;

DETAILED DESCRIPTION OF THE INVENTION

Figure 2:
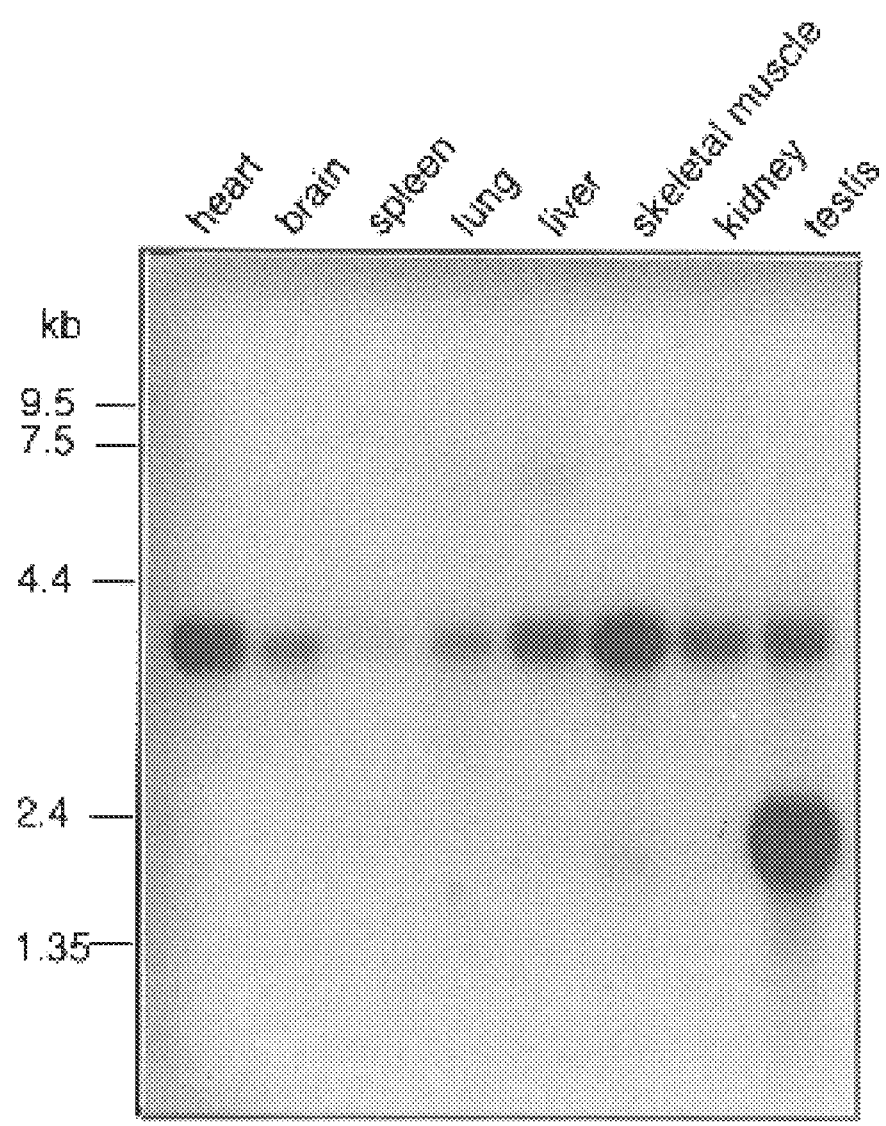
FIG. 2 is the result of the northern blotting of various mouse organs with MKK7 which is performed in Example 3.

According to the present invention, there is provided a substantially pure MAPK (mitogen-activated protein kinase) kinase derived from a vertebrate, wherein the MAPK kinase has the following characteristics:

(a) the MAPK kinase is activated by a stimulus induced by TNF-α and/or by a stimulation of Fas antigen;

(b) the MAPK kinase activates SAPK/JNK; and (c) the MAPK kinase does not activate p38.

For easy understanding of the present invention, the essential features and various preferred embodiments of the present invention are enumerated below.

1. A substantially pure MAPK (mitogen-activated protein kinase) kinase derived from a vertebrate, wherein the MAPK kinase has the following characteristics:

(a) the MAPK kinase is activated by a stimulus induced by TNF-α and/or by a stimulation of Fas antigen;

(b) the MAPK kinase activates SAPK/JNK; and (c) the MAPK kinase does not activate p38.

2. The MAPK kinase according to item 1 above, which has an amino acid sequence selected from the group consisting of SEQ ID NOs: 2, 4 and 6; or has a variant amino acid sequence which is obtained by deletion or substitution of one or several amino acid residue(s) of the amino acid sequence, or by addition of one or several amino acid residue(s) to the amino acid sequence.

3. A DNA coding for the MAPK kinase of item 1 or 2 above.

4. The DNA according to item 3 above, which has a nucleotide sequence selected from the group consisting of SEQ ID NOs: 1, 3 and 5; or has a nucleotide sequence which is capable of hybridization with a DNA having the nucleotide sequence under stringent conditions.

5. A replicable recombinant DNA which comprises a replicable expression vector and, operably inserted therein, the DNA of item 3 or 4 above.

6. A cell of a microorganism or a cell culture, which is transformed with the replicable recombinant DNA of item 5 above.

7. A polypeptide, which is a dominant negative form of the MAPK kinase of item 1 or 2 above, wherein the polypeptide lacks only a kinase activity of the MAPK kinase, and the polypeptide inhibits the activation of SAPK/JNK by the MAPK kinase which is induced by TNF-α.

8. The polypeptide according to item 7 above, which has an amino acid sequence of SEQ ID NO: 10; or has a variant amino acid sequence which is obtained by deletion or substitution of one or several amino acid residue(s) of the amino acid sequence, or by addition of one or several amino acid residue(s) to the amino acid sequence.

9. A DNA coding for the polypeptide of item 7 or 8 above.

10. The DNA according to item 9 above, which has a nucleotide sequence of SEQ ID NO: 9; or has a nucleotide sequence which is capable of hybridization with a DNA having the nucleotide sequence under stringent conditions.

11. A replicable recombinant DNA which comprises a replicable expression vector and, operably inserted therein, the DNA of item 9 or 10 above.

12. A cell of a microorganism or a cell culture, transformed with the replicable recombinant DNA of item 11 above.

13. The MAPK kinase according to item 1 or 2 above, which is in an activated form, wherein a serine residue and/or a threonine residue in the MAPK kinase, which contribute/contributes to activation of the MAPK kinase upon being phosphorylated, are/is phosphorylated.

14. A method for screening a substance having the capability to inhibit the activity of a MAPK kinase, which comprises:

contacting a sample with at least one kinase selected from the group consisting of the MAPK kinase of item 1 or 2 above and the activated form of MAPK kinase of item 13 above, together with SAPK/JNK;

assessing the inhibition of activation of SAPK/JNK; and detecting the substance by using the inhibition as a criterion.

15. An antibody capable of binding specifically to the MAPK kinase of item 1 or 2 above, or to the activated form of MAPK kinase of item 13 above.

Hereinbelow, the present invention is described in detail.

In the present invention, with respect to the nucleotide sequences, A represents adenine, C represents cytosine, G represents guanine and T represents thymine.

In the present invention, with respect to the amino acid sequences shown in 3-letter abbreviation, Ala represents an alanine residue, Arg represents an arginine residue, Asn represents an asparagine residue, Asp represents an aspartic acid residue, Cys represents a cysteine residue, Gln represents a glutamine residue, Glu represents a glutamic acid residue, Gly represents a glycine residue, His represents a histidine residue, Ile represents an isoleucine residue, Leu represents a leucine residue, Lys represents a lysine residue, Met represents a methionine residue, Phe represents a phenylalanine residue, Pro represents a proline residue, Ser represents a serine residue, Thr represents a threonine residue, Trp represents a tryptophan residue, Tyr represents a tyrosine residue and Val represents a valine residue.

In the present invention, with respect to the amino acid sequences shown in 1-letter abbreviation, A represents an alanine residue, R represents an arginine residue, N represents an asparagine residue, D represents an aspartic acid residue, C represents a cysteine residue, Q represents a glutamine residue, E represents a glutamic acid residue, G represents a glycine residue, H represents a histidine residue, I represents an isoleucine residue, L represents a leucine residue, K represents a lysine residue, M represents a methionine residue, F represents a phenylalanine residue, P represents a proline residue, S represents a serine residue, T represents a threonine residue, W represents a tryptophan residue, Y represents a tyrosine residue and V represents a valine residue.

In the present invention, the term "polypeptide" means any substance which is generally understood as a peptide, an oligopeptide, a polypeptide, a protein and the like by those skilled in the art. Therefore, the polypeptide may be a natural protein, or a polypeptide or peptide obtained by chemical synthesis or recombinant DNA technology, and it may or may not be subjected to post-translational modification, such as glycosylation or phosphorylation.

The term "MAPK kinase" used in the present invention means a group of protein kinases participating in a MAP kinase cascade which activates a MAP kinase through phosphorylation thereof. Examples of MAPK kinases known in the art include MKK3, MKK4 and MKK6. For example, MKK4 phosphorylates the 180th Thr and 182nd Tyr of a MAP kinase called p38, and it also phosphorylates the 183rd Thr and 185th Tyr of another MAP kinase called SAPK/JNK, so that both MAP kinases are activated by MKK4. MKK7, which is the novel MAPK kinase of the present invention, is also an enzyme which activates a MAP kinase through phosphorylation thereof; however, unlike MKK4 mentioned above, MKK7 is specific for SAPK/JNK and it does not activate p38.

In the present invention, a "variant amino acid sequence which is obtained by deletion or substitution of one or several amino acid residue(s), or by addition of one or several amino acid residue(s)" is an amino acid sequence of a naturally occurring variant amino acid sequence resulting from an allelic mutation or a spontaneous mutation, or an artificial amino acid sequence obtained by mutagenesis or gene recombination. In addition, the presence of an alternatively spliced form of MKK7 has been confirmed by the present inventors at a cDNA level and by western blotting, and the alternatively spliced form of MKK7 is also included in the MKK7 of the present invention. Amino acids in the N-terminal region and C-terminus of mouse MKK7 are deleted in the alternatively spliced form of mouse MKK7, but such an amino acid sequence also exhibits the characteristics of the novel MAPK kinase of the present invention (the sequences are shown in SEQ ID NOs: 5 and 6).

All of the amino acid sequences of the present invention are polypeptides which exhibit the activity of the novel MAPK kinase of the present invention, and an amino acid sequence which has lost the MAPK kinase activity is excluded from the present invention even when only one amino acid residue of the amino acid sequence is modified. Therefore, "a variant amino acid sequence which is obtained by deletion or substitution of one or several amino acid residue(s), or by addition of one or several amino acid residue(s)" is an amino acid sequence which conserves a region consisting of the kinase domains I to XI (a region common to serine/threonine kinases which is responsible for the activity of the kinases) in the MAPK kinase of the present invention shown in SEQ ID NOs: 2, 4 or 6, and which particularly contains fifteen amino acid residues in the kinase domains which are critical for its activity {Hanks, S. K. and Quinn, A. M., *Method in Enzymology, vol.* 200, pp. 38–62 (1992)}. Illustratively stated, with-respect to the mouse MKK7 of the present invention, the kinase region thereof consists of the 136th to 396th amino acids of SEQ ID NO: 4, and the fifteen critical amino acid residues therein are the 143rd Gly, the 145th Gly, the 150th Val, the 165th Lys, the 175th Glu, the 259th Asp, the 261st Lys, the 264th Asn, the 277th Asp, the 279th Gly, the 302nd Pro, the 303rd Glu, the 320th Asp, the 325th Gly and the 384th Arg. The kinase region and fifteen critical amino acid residues therein are also present in the human MKK7 (SEQ ID NO: 2) of the present invention.

In the present invention, a "nucleotide sequence which is capable of hybridization with a DNA under stringent conditions" is a nucleotide sequence which is highly homologous to the DNA of the present invention and can be identified under conditions at which a non-specific hybridization is reduced, that is, under conditions provided by changing the temperature and salt concentration used in the washing process performed after the hybridization process. Illustratively stated, the nucleotide sequences of the present invention are those which hybridize with the DNA encoding MKK7 in the presence of 1.0×SSC and 0.1% SDS at 55° C., in which the specificity between the polynucleotides is assured. Such a nucleotide sequence has at least 80% homology with the nucleotide sequence of the DNA encoding the MAPK kinase of the present invention.

In the present invention, a polypeptide of a "dominant negative form" is an MKK7 polypeptide which lacks only the kinase activity, and it is obtained by mutating a part of the kinase domains of MKK7. A dominant negative polypeptide is also called a kinase negative, and its coexistence with MKK7 results in the inhibition of the kinase activity of MKK7. MKK7KL is one example of the dominant negative polypeptide of the present invention which inhibits the SAPK/JNK-activating activity of MKK7, and it has an amino acid sequence obtained by substituting the 165th Lys (K) by Leu (L) (the nucleotide and amino acid sequences of MKK7KL are shown in SEQ ID NOs: 9 and 10, respectively). The dominant negative form of the MAPK kinase of the present invention is not limited to the above-mentioned MKK7KL, and a polypeptide lacking only the kinase activity can be easily prepared based on the human and mouse nucleotide sequences and amino acid sequences shown in SEQ ID NOs: 1 to 6. Further, the dominant negative polypeptide of the present invention is not limited to the amino acid sequence of MKK7KL shown in SEQ ID NO: 10, and this sequence can be further modified as long as the function of the dominant negative polypeptide is maintained. Illustratively stated, the dominant negative polypeptide can be a variant of MKK7KL obtained by deletion or substitution of one or several amino acid residue (s), or addition of one or several amino acid residue(s) in the amino acid sequence shown in SEQ ID NO: 10, as long as the kinase region of MKK7KL is conserved.

For making more clear the essential features of the present invention, the technical features of the present invention are described in detail below.

In order to clone a novel MAPK kinase gene, a Xenopus oocyte cDNA library was screened by cross hybridization using human MKK3 (a MAPK kinase known in the art) gene as a probe. As a result, the present inventors successfully cloned a novel Xenopus MAPK kinase fragment shown in SEQ ID NOs: 7 and 8, which is similar to a Drosophila MAPK kinase called Hep. Hep is an enzyme which plays an important role in embryonic morphogenesis of Drosophila {Glise, B. et al., *Cell,* 83: 451–461 (1995)}, and no mammalian MAPK kinase corresponding to Hep has been conventionally known. The amino acid sequence homologies between Hep and human MKK3 and between Hep and MKK4 are 48% and 56%, respectively.

The presence of a Hep-homologous MAPK kinase in an organism other than Drosophila suggested the possibility for a similar MAPK kinase to exist in mammals. In order to clone a mammalian kinase which is homologous to Hep, screening of a mouse brain cDNA library was performed using the above-mentioned novel Xenopus MAPK kinase gene fragment as a probe. As a result, the present inventors successfully cloned a novel mouse MAPK kinase shown in SEQ ID NOs: 3 and 4 which is structurally belonging to the MAPK kinase family.

Unlike any other mammalian MAPK kinases known in the art, the mouse MAPK kinase of the present invention has highest homology with Hep of Drosophila. The amino acid sequence homology between the kinase domain of the novel mouse MAPK kinase and that of Hep of Drosophila is 69%, but the homology is only 53% between that of the novel mouse MAPK kinase and mouse SEK1/MKK4. From these results, it is apparent that the MAPK kinase successfully cloned by the present inventors is a molecule which is more similar to Hep than other MAPK kinases (see FIG. 1). Therefore, this MAPK kinase is considered to be a mammalian homologue of Hep.

The present inventors named this novel MAPK kinase "MKK7". An international deposit of *E. coli* transformed with a plasmid vector encoding mouse MKK7, namely, *E. coli*: DH5-pBluemMKK7 (Deposit number: FERM BP-6397), was made with National Institute of Bioscience and Human-Technology, Agency of Industrial Science and Technology {1–3, Higashi 1-chome, Tsukuba-shi, Ibaraki-ken, Japan (Postal Code No. 305-8566)} on Jun. 26, 1997 (original deposit date).

In addition, based on the nucleotide sequence of the mouse MKK7, a human EST database was searched for human MKK7 clones, and two candidates (both of which are cDNAs obtained from randomly extracted human mRNA) have been identified. The present inventors have successfully cloned the whole human MKK7 shown in SEQ ID NOs: 1 and 2 from human heart mRNAs by performing 5' RACE (rapid amplification of cDNA end) method, 3' RACE method, and PCR method based on the nucleotide sequences obtained from the database. Amino acid sequence homology between mouse MKK7 and human MKK7 was 91%.

An international deposit of *E. coli* transformed with a plasmid vector encoding human MKK7, namely, *E. coli*: DH5-pTrCHisBhMKK7 (Deposit number: FERM BP-6398), was made with National Institute of Bioscience and Human-Technology, Agency of Industrial *Science and Technology* {1–3, Higashi 1-chome, Tsukuba-shi, Ibaraki-ken, Japan (Postal Code No. 305-8566)} on Aug. 8, 1997 (original deposit date).

Next, the present inventors performed northern blotting to observe the expression of mouse MKK7 in vivo. The expression of mouse MKK7 mRNA was confirmed in most organs, and strong expression was detected in heart and skeletal muscles (see FIG. 2).

Figure 3:
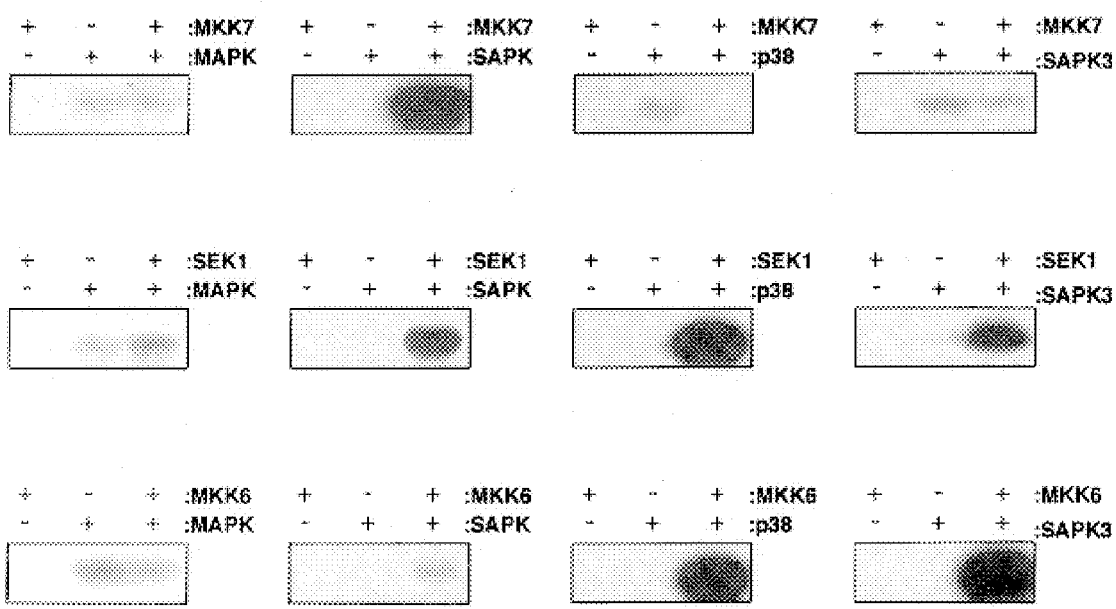
FIG. 3 is the result of the SDS-polyacrylamide gel electrophoresis performed in Example 5 to confirm the substrate specificity of mouse MAPK kinases (MKK7, MKK6 and SEK1) for MAP kinases (MAPK, SAPK, p38 and SAPK3), and in FIG. 3, a plus (+) indicates the addition of a particular kinase, and a minus (−) indicates the absence of a particular kinase.

Since the primary structure of MKK7 revealed that it virtually belongs to the MAPK kinase family, the MAP kinase-activating activity of the MAPK kinase was measured using various MAP kinases as a substrate for the MAPK kinase. In addition to MKK7, MKK6 and SEK1 were used as the MAPK kinase, and MAPK, SAPK, p38 and SAPK3 were used as the MAP kinase. A MAPK kinase gene and a MAP kinase gene were cotransfected to a cell in different combinations, and the activity of the MAP kinase in vivo was determined by measuring the amount of a substrate (for the transfected MAP kinase) phosphorylated by the cotransfected cells. As a result, it has been found that, unlike SEK1 or MKK6, the mouse MKK7 activates only SAPK, and does not activate p38 or SAPK3 (see FIG. 3). Moreover, the results suggest the possibility for MKK7 to suppress the activity of p38. From this experiment, it has become apparent that the optimum pH for MKK7 is in the range of from pH 7 to 8, and MKK7 is deactivated at 70° C. or higher.

Figure 4:
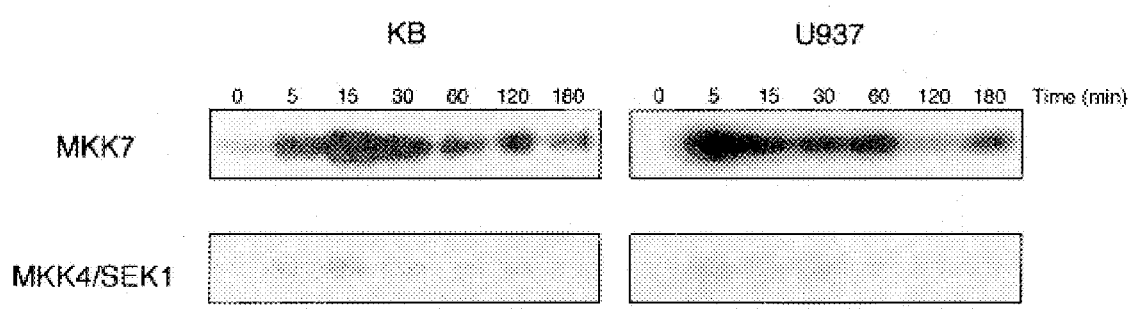
FIG. 4 is the result of the SDS-polyacrylamide gel electrophoresis performed in Example 6, which shows that mouse MKK7 is activated by TNF-α, but mouse SEK1/MKK4 is not activated by TNF-α.

From in vitro experimental results, SEK1/MKK4 has been considered to be a MAPK kinase located in the upstream of SAPK/JNK in the MAP kinase signal cascade; however, contrary to the fact that SAPK/JNK is strongly activated by TNF-α, the activation of SEK1/MKK4 is independent of a stimulus induced by TNF-α (see FIG. 4). Therefore, the existence of MAPK kinases besides SEK1/MKK4 in the upstream of SAPK/JNK in vivo has been considered. From the above-results, it has become apparent that MKK7 of the present invention is the MAPK kinase in the upstream of SAPK/JNK, which participates in the following signal cascade induced by TNF-α:

In order to substantiate that MKK7 is a true activator for SAPK/JNK in the upstream of SAPK/JNK, the present inventors performed an experiment to confirm that the activation of mouse MKK7 is induced by TNF-α (see FIG. 4). Next, the present inventors prepared and expressed the dominant negative form of MKK7 in a cell. The activation of SAPK/JNK which is dependent on a stimulus induced by TNF-α was suppressed in a cell expressing the dominant negative form of MKK7 (see FIG. 5). From the results of the above-mentioned experiments, MKK7 was substantiated to be a kinase which plays an important role in the signal transduction pathway in vivo starting from TNF-α and leading to SAPK/JNK.

From the recent data showing that SAPK/JNK and p38 participate in apoptosis {Xia, Z. et al., *Science*, 270: 1326–1331 (1995); Verheij, M. et al., *Nature*, 380: 75–79 (1996); and Santana, P. et al., *Cell*, 86: 189–199 (1996)}, and from a report on an apoptosis-inducing MAPKK kinase called ASK1 {Ichijo, H. et al., *Science*, 257: 90–94 (1997)}, it is considered that there is a relation between the MAP kinase cascade and apoptosis. Based on these reports, the present inventors stimulated Fas antigen to study the possibility for MKK7 to participate in apoptosis. Fas antigen (also known as APO-1 or CD95) is a receptor capable of inducing apoptosis and is a type I transmembrane protein belonging to TNF/NGF receptor family {Suda, T. et al., *Cell*, 75: 1169–1178 (1993)}. The Fas antigen of a cell was stimulated with an anti-Fas antibody (CH-11), and the activities of SAPK/JNK and MKK7 were determined. As a result, it has become apparent that both SAPK/JNK and MKK7 are activated by a signal induced from the Fas antigen (see FIG. 6). This result suggests that MKK7, together with SAPK/JNK, participates in the transduction of apoptotic signals from the Fas antigen.

A cDNA cloned in the present invention encodes the novel MAPK kinase MKK7 which is activated by a stimulus induced by TNF-α and/or by a stimulation of Fas antigen, and which in turn activates SAPK/JNK, but does not activate p38. The nucleotide sequence of the cloned DNA may be ligated to an expression vector capable of expression in a host cell, in which the expression vector contains transcription regulatory sequences, such as a promoter, an operator and an enhancer; termination sequences; and other regulatory sequences which regulate the expression of MKK7. There is no particular limitation to the expression vector used in the present invention as long as the vector can be introduced into a host cell and expressing the DNA inserted therein. The expression vector may be of either a prokaryotic origin or an eukaryotic origin, and virus vectors and plasmid vectors are typically used.

A cell of a microorganism or a cell culture, which is transformed with the replicable recombinant DNA containing any one of the nucleotide sequences of the present invention can be prepared by transformation, that is, a method for introducing a nucleotide sequence into a cell. Examples of transformation methods include transfection, electroporation, microinjection and lipofection, but the method employed in the present invention is not limited to those mentioned above. In addition, by using the recombinant DNA technology mentioned above, it is possible to regulate the expressian of MKK7. For example, an appropriate regulatory factor is ligated to the MKK7 sequence to thereby obtain a recombinant DNA, and then, a host cell is transformed with the recombinant DNA to achieve a desired expression. The copy number of the nucleotide sequence, the efficiency of transcription, the efficiency of translation and post-translational modification can be controlled by changing a microorganism or a cell culture used as a host cell and by changing the construction of the recombinant DNA.

The MKK7 polypeptide and DNA of the present invention can be advantageously used for identifying a substance which is capable of functional regulation of MKK7 in the MAP kinase cascade. The above-mentioned "functional regulation of MKK7" includes both activation of MKK7 and inhibition of MKK7, and especially, a substance capable of inhibiting the activation of MKK7 has various utilities. Such a substance is effective for treating or preventing diseases in which an excess activation or inhibition of the MAP kinase cascade by MKK7 participates in at least a part of the mechanism responsible for the onset of the disease. In the present invention, the participation of MKK7 in the TNF-α-induced intracellular signal transduction has been substantiated by the suppression of the TNF-α-induced activation of SAPK/JNK by the dominant negative form of MKK7. From the fact that TNF-α induces or relates to the development of autoimmune diseases and inflammatory reactions, MKK7 seems to play a critical role in the above-mentioned diseases.

As mentioned above, the present invention revealed that MKK7 is activated by a stimulation of Fas antigen, and the activated MKK7 in turn activates SAPK/JNK. This observation suggests the possibility for MKK7 to participate in the transduction of apoptosis signals induced by TNF-α or a stimulation of Fas antigen. Examples of diseases in which a suppression of apoptosis may result in the treatment of the diseases include cutaneous diseases, such as GVHD and toxic epidermal necrolysis (TEN); proliferative nephritis (such as IgA nephritis, purpuric nephritis and lupus nephritis); and fulminant hepatitis. On the other hand, tumor is an example of a disease in which an induction of apoptosis may result in the treatment of the disease. It is also known that MKK7 is activated by an environmental stress, and the use of MKK7 for treating diseases (such as ischemic attack) caused by stresses, and burns caused by heat and radiation (such as UV, X-ray, γ-ray and β-ray) has been taken into consideration.

With respect to the method for screening a substance which specifically reacts with MKK7 of the present invention (particularly a substance having the capability to inhibit the activity of MKK7), for example, the experimental system of Example 5 can be employed. Illustratively stated, by using the reaction system "+MKK7 +SAPK +c-Jun" shown in FIG. 3, a specific inhibitor for MKK7 can be obtained by detecting a substance which only suppresses the phosphorylation of c-Jun and exhibits no effect on other reaction systems. Alternatively, a method for identifying a substance capable of regulating a signal starting from a cell surface receptor, such as TNF-α receptor and Fas antigen, can be employed. In this method, the effects of a substance on the activity of MKK7 can be determined by (1) contacting a cell expressing a receptor and MKK7 with a sample substance, (2) subsequently contacting the cell with a ligand for the receptor, and (3) measuring the activity of SAPK/JNK. The screening methods of the present invention is not limited to these methods. In the above-mentioned methods, MKK7 is activated naturally by the phosphorylation in a cell, but alternatively, the screening can be performed by vigorously activating MKK7 in accordance with the phosphorylation method of Example 9. In an activated MKK7, serine and/or threonine residues necessary for the MAPK kinase activity are/is phosphorylated. Since there is a possibility for non-phosphorylated MKK7 to exhibit the activity (even though it is very weak), the screening method can be performed by using a large amount of non-phosphorylated MKK7.

The sample substances used for screening a substance having the capability to inhibit the activity of MKK7 can be either a high molecular compound or an orally administrable low molecular compound. A specific inhibitor for MKK7 obtained by the screening method can be used, for example, as a specific anti-inflammatory drug or as a drug for treating autoimmune diseases (such as rheumatoid arthritis). Such a drug only blocks a particular function of TNF-α, and exhibits no effect on other functions of TNF-α.

Based on the nucleotide sequence of MKK7 of the present invention, a complementary sequence thereof, that is, a specific antisense for MKK7, can be prepared with ease. An antisense mentioned herein is a polynucleotide (DNA, RNA and the like) complementary to at least a part of the mRNA or DNA encoding MKK7 which is capable of inhibiting the transcription or translation of MKK7. Illustratively stated, a polynucleotide which can be used as an antisense is a polynucleotide sequence having 100% homology to at least twelve contiguous nucleotides of the nucleotide sequence encoding MKK7. The effect of the antisense can be confirmed by using the transformants of the present invention. The MKK7 gene can be advantageously used in gene therapy for treating various diseases, including cancer, autoimmune disease, allergic disease, and inflammatory response. Gene therapy is a therapy in which a gene or a cell transformed with the gene is administered intracorporeally to a patient for treating a disease.

The MKK7 protein or DNA of the present invention can be used for diagnoses. The MKK7 protein can be produced in a large amount by using the cells transformed with the MKK7 gene of the present invention, and using the produced protein, a monoclonal antibody specific for MKK7 can be obtained with ease. As an immunizing antigen, the whole MKK7 protein of human or mouse, or a fragment consisting of at least five contiguous amino acid residues of the MKK7 amino acid sequence can be employed. Examples of antibodies of the present invention include not only a complete antibody, but also fragments containing the antigen-binding sites, such as Fab fragment, F(aB')$_2$ fragment and scFv fragment. By using the antibody of the present invention, it becomes possible to construct a system for detecting the MKK7 protein in cells or tissues by ELISA or RIA, or western blotting. Such a system for detecting MKK7 can be used for diagnosis. Further, a probe specific for MKK7 mRNA is capable of detecting the expression of MKK7 in cells or tissues (see Example 3 and FIG. 2), and such a probe can be used for a diagnostic assay.

BEST MODE FOR CARRYING OUT THE INVENTION

Hereinbelow, the present invention will be described in more detail with reference to the following Examples, but they should not be construed as limiting the scope of the present invention.

EXAMPLE 1
Cloning of Mouse MKK7 Gene

First, a method for cloning the novel mouse MKK7 gene of the present invention will be explained below. Using the whole coding region of human MKK3 gene as a probe, "*Xenopus laevis,* oocyte 5'-STRETCH cDNA library" (manufactured and sold by CLONTECH Laboratories, Inc., USA) was screened by plaque hybridization, thereby obtaining a hybridized filter in which phage DNAs on the filter were hybridized with human MKK3 gene. The obtained filter was washed with a washing buffer containing 2×SSC and 0.1% SDS at 42° C. As a result, 10 positive clones were obtained among the total of 120,000 phage DNAs subjected to hybridization. Nucleotide sequences of the obtained positive clones were analyzed and three clones encoding a novel kinase which is homologous to *Drosophila hep* were isolated. The novel Xenopus kinase gene fragment was obtained, and the nucleotide sequence thereof is shown in SEQ ID NO: 7.

Next, using the fragment of the novel *Xenopus laevis* kinase gene as a probe, "mouse brain cDNA library Uni-ZapT™ XR vector" (manufactured and sold by Stratagene Cloning Systems, USA) was screened by plaque hybridization, thereby obtaining a hybridized filter in which phage DNAs on the filter were hybridized with the novel Xenopus kinase gene. The obtained filter was washed with a washing buffer containing 2×SSC and 0.1% SDS at 42° C. As a result, 11 positive clones were obtained among 200,000 phage DNAs subjected to hybridization. Nucleotide sequences of the obtained positive clones were analyzed and a nucleotide sequence encoding a novel kinase protein, which is shown in SEQ ID NO: 3, was obtained. The protein coded by the obtained nucleotide sequence was named "MKK7". Another clone shown in SEQ ID NO: 5 was obtained together with MKK7, and this clone encoded an amino acid sequence in which the N-terminal region and C-terminus of MKK7 are deleted. This clone was deduced to be a clone resulting from an RNA splicing occurring at a different site from that of the clone shown in SEQ ID NO: 3 (i.e., an alternative splicing product).

Mouse MKK7 gene was cut-out from Uni-Zap™ XR vector of the positive clone and inserted into Blue-script Vector to prepare a recombinant plasmid containing mouse MKK7 gene. Subsequently, *E. coli* was transformed with the prepared recombinant plasmid, thereby obtaining a transformant containing the mouse MKK7 gene. An international deposit of the obtained transformant, namely, *E. coli*: DH5-pBluemMKK7 (Deposit number: FERM BP-6397), was made with National Institute of Bioscience and Human-Technology, Agency of Industrial Science and Technology {1–3, Higashi 1-chome, Tsukuba-shi, Ibaraki-ken, Japan (Postal Code No. 305-8566)} on Jun. 26, 1997 (original deposit date).

EXAMPLE 2

Cloning of Human MKK7 Gene

Using the nucleotide sequence of the mouse MKK7 gene obtained in Example 1, a homology search was performed with respect to the EST database (which is a database publishing cDNA sequences obtained from randomly extracted RNAs derived from various human and mouse tissues). Two human-derived clones (*Homo sapiens* cDNA clones 665682 and 363521) which are homologous to the mouse MKK7 gene were found in the database. Clone 665682 was a fragment (corresponding to the 961st to 1,190th nucleotides of SEQ ID No: 1) which is highly homologous to the N-terminal region of mouse MKK7, and clone 363521 was a fragment (corresponding to the 360th to 820th nucleotides of SEQ ID No: 1) which is highly homologous to the C-terminal region of mouse MKK7. The nucleotide sequence of human MKK7 gene was determined using the nucleotide sequences of these two clones. Illustratively stated, human heart poly A$^+$ RNA (manufactured and sold by CLONTECH Laboratories, Inc., USA) was used as a source of human RNA, and based on the sequence information obtained from the database, the nucleotide sequence of human MKK7 gene was determined by means of 5' RACE System and 3' RACE System (manufactured and sold under the brand name of GIBCO BRL, USA) in accordance with protocols attached thereto. As a primer for synthesizing cDNA by 5' RACE method, synthetic oligonucleotide 5'-TTTGGTCTCTTCCTGTGATC-3'(SEQ ID NO:12), was used. For actually cloning the 5'-end of MKK7 gene, PCR was conducted 15 cycles using AUAP primer attached to the 5' RACE System and synthetic oligonucleotide 5'-TGCTTAACGGCAATGACGTG-3', thereby obtaining a PCR product. Subsequently, further PCR was conducted 25 cycles using 1 μl of the obtained PCR product as a template, and the AUAP primer and synthetic oligonucleotide 5'-TTGATTTCTGCCTGGTAGCG-3'(SEQ ID NO:13), as a primer set, to thereby clone a gene comprising the 5'-end of human MKK7 gene. With respect to the 3' RACE method, cDNA was synthesized in accordance with the protocol attached to the 3' RACE System, and then, PCR was conducted 34 cycles using AUAP primer attached to the 3' RACE System and synthetic oligonucleotide 5'-CAGTCCTTCGTCAAAGACTG-3'(SEQ ID NO:14), thereby obtaining a PCR product. Subsequently, further PCR was conducted 25 cycles using 1 μl of the obtained PCR product as a template, and the AUAP primer and synthetic oligonucleotide 5'-CAGTCCTTCGTCAAAGACTG-3' (SEQ ID NO:15) as a primer set, to thereby clone a gene comprising the 3'-end of human MKK7 gene. With respect to the sequence in-between the 5' and 3' regions of human MKK7 gene obtained above, PCR was conducted 34 cycles using synthetic oligonucleotides 5'-CGCTACCAGGCAGAAATCAA-3'(SEQ ID NO:16) and 5'-TTTGGTCTCTTCCTGTGATC-3'(SEQ ID NO:17) respectively as 5' and 3' primers. The cDNA employed in the above-mentioned 5' RACE method was used as a template. As a result, whole human MKK7 clone was obtained. The nucleotide sequence of the obtained clone, that is, the whole nucleotide sequence of human MKK7 gene, was determined and shown in SEQ ID No: 1.

The above-mentioned whole nucleotide sequence of human MKK7 gene was inserted into *E. coli* expression vector pTrCHisB (manufactured and sold by Invitrogen Corporation, The Netherlands), thereby obtaining a recombinant plasmid, and *E. coli* (DH5) was transformed with the recombinant plasmid, to thereby obtain a transformant containing the human MKK7 gene. An international deposit of the obtained transformant, namely, *E. coli*: DH5-pTrCHisBhMKK7 (Deposit number: FERM BP-6398), was made with National Institute of Bioscience and Human-Technology, Agency of Industrial Science and Technology {1–3, Higashi 1-chome, Tsukuba-shi, Ibarakiken, Japan (Postal Code No. 305-8566)} on Aug. 8, 1997 (original deposit date).

EXAMPLE 3

Northern Hybridization

In order to examine the mRNA expression of the novel MAPK kinase of the present invention in various mouse organs (i.e., heart, brain, spleen, lung, liver, skeletal muscle, kidney and testis), a northern hybridilization of "Mouse Multiple Tissue Northern Blot" (manufactured and sold by CLONTECH Laboratories, Inc., USA) was performed using the coding region of mouse MKK7 gene as a probe. The probe was radiolabeled with [α-$^{32}$P] CTP (manufactured and sold by Amersham International, England) by using deoxy-nucleotidyl transferase (manufactured and sold by TOYOBO Co., Ltd, Japan). The hybridized filter in which mouse mRNAs thereon were hybridized with the mouse MKK7 gene was washed twice with a buffer containing 2×SSC and 0.04% SDS at room temperature for 20 minutes, and further washed twice with a buffer containing 0.1×SSC and 0.1% SDS at 50° C. for 20 minutes. After washing the filter, the radioactivity of the hybrized mRNAs was measured by autoradiography. The resultant autoradiogram is shown in FIG. 2.

As apparent from FIG. 2, the MAPK kinase mRNA is expressed in all of the organs examined, and especially strong expression was detected in heart and skeletal muscle.

EXAMPLE 4
Preparation of a Dominant Negative Form of MKK7

A dominant negative form of MKK7 was prepared by substituting the 165th Lysine (K) of mouse MKK7 with leucine (L). Illustratively stated, the dominant negative form of MKK7 gene was prepared using synthetic oligonucleotide:

5'-CAGGGCACATCATTGCTGTTCTGCAGATGCGG CGCTCTGGGAAC-3'(SEQ ID NO:18)

and Transformer Site-Directed Mutagenesis Kit (manufactured and sold by CLONTECH Laboratories, Inc., USA) in accordance with the protocol attached thereto. The protein coded by the prepared gene was named "MKK7KL". The nucleotide sequence of the prepared dominant negative form of MKK7 gene is shown in SEQ ID NOs: 9 and 10.

EXAMPLE 5
(1) Construction of Various Expression Vectors and Preparation of Various Recombinant Proteins Using the Same The following synthetic oligonucleotides:

5'-GATCGCCGCCACCATGTACCCATACGACGTCCC AGATTACGCTCCCGGGAGATCTG-3'(SEQ ID NO:19) and

5'-AATTCAGATCTCCCGGGAGCGTAATCTGGGAC GTCGTATGGGTACATGGTGGCGGC-3'(SEQ ID NO:20)

were respectively introduced into BglII site and EcoRI site of mammalian expression vector pSRα456, thereby obtaining vector pSRα-HA1. Vector pSRα-MKK7KL was constructed by introducing the coding region of the dominant negative form of MKK7 gene obtained in Example 4 into the above-mentioned sites of vector pSRα456. The coding region of mouse SAPKα gene was introduced into BglII site of vector pSRα-HA1 to construct expression vector pSRα-HA-SAPKα.

The following expression plasmids were constructed for preparing various MAPK kinases. Mouse SEK1 gene was inserted into vector pGEX-2T (manufactured and sold by Pharmacia Biotech AB, Sweden) to thereby construct an expression plasmid for GST-SEK1. Human MKK6 gene and mouse MKK7 gene were separately inserted into vector pET28 (manufactured and sold by Novagen Inc., USA) to thereby individually construct the expression plasmids for His-MKK6 and His-MKK7.

The following expression plasmids were constructed for preparing various MAP kinases. Xenopus MAPK gene was inserted into vector pTrcHisC (manufactured and sold by Invitrogen Corporation, The Netherlands) to thereby construct an expression plasmid for His-MAPK. Mouse SAPKαgene, p38 gene and SAPK3 gene were individually inserted into vector pET28 (manufactured and sold by Novagen Inc., USA) to thereby construct the expression plasmids for His-SAPKα, His-p38 and His-SAPK3. Human c-Jun gene fragment encoding the 1st to 79th amino acids of whole Jun was inserted into vector pGEX-3X (manufactured and sold by Pharmacia Biotech AB, Sweden) to thereby construct an expression plasmid for GST-cJun.

The above-mentioned expression plasmids were individually introduced into E. coli and the proteins expressed in E. coli were purified therefrom. With respect to the GST (glutathione-S-transferase)-fusion proteins, the proteins were individually purified by means of Glutathione Sepharose 4B column (manufactured and sold by Pharmacia Biotech AB, Sweden). With respect to the His (histidine cluster)-tagged proteins, the proteins were individually purified by means of pET Expression Systems (manufactured and sold by Novagen Inc., USA) in accordance with the protocol attached thereto.
(2) Specific Activation of SAPK by MKK7

0.1 µg of a MAPK kinase (His-MKK7, GST-SEK1 and His-MKK6 were separately used) and 0.5 µg of a MAP kinase (His-MAPK, His-SAPK, His-p38 and His-SAPK3 were separately used), both prepared in item (1) above, were incubated with 10 µl of a solution containing 100 µM ATP, 20 mM $MgCl_2$, 2 mM EGTA and 20 mM Tris-HCl (pH 7.5) at 30° C. for 30 minutes, to thereby activate the MAP kinase. Subsequently, 5 µl of a solution containing a substrate for the MAP kinase and 1 µCi of [$\gamma$-$^{32}$P] ATP (manufactured and sold by Amersham International, England) was added to the mixture, and further incubated at 20° C. for 20 minutes. As a substrate for the MAP kinase, 3 µg of myelin basic protein (MBP) was used for MAPK and SAPK3, 3 µg of GST-cJun (1–79) was used for SAPK, and 3 µg of ATF-2 was used for p38. The MBP used as the substrate was obtained by purifying Brain Acetone Powder (manufactured and sold by Sigma, USA), and ATF-2 was a kind gift of Dr. Suzanne J. Baker and Dr. Tom Curran (St. Jude Children's Research Hospital). After incubation, a sample was obtained from each incubated mixture and resolved on SDS-polyacrylamide gel electrophoresis. Then, the radioactivity of each of MBP, c-Jun and ATF-2 was detected by autoradiography. As apparent from FIG. 3, mouse MKK7 did not activate p38 and SAPK3, but specifically activated SAPK, leading to the phosphorylation of c-Jun. The results suggest the possibility for mouse MKK7 to suppress the activity of p38. On the other hand, mouse SEK1 activated all of SAPK, p38 and SAPK3, and MKK6 activated p38 and SAPK3, but did not activate SAPK.

EXAMPLE 6
Activation of MKK7 by TNF-α

KB cells were cultured in Dulbecco's modified Eagles medium (DMEM) containing 10% bovine serum, and the cultured cells were stimulated with 20 ng/ml human TNF-α (manufactured and sold by BECTON DICKINSON AND COMPANY, USA, under the brand of Collaborative Biomedical Products). U937 cells were cultured in RPMI 1640 medium containing 10% fetal bovine serum, and the cultured cells were stimulated with 100 ng/ml human TNF-α. The cells were sampled from each cell culture 5, 15, 30, 60, 120 and 180 minutes after the start of the stimulation to thereby prepare cell extracts. The cell extracts were prepared as follows. The sampled cells were suspended in 0.7 M NaCl solution and washed once with ice-cold HEPES-buffered saline. Subsequently, the washed cells were homogenized in a buffer containing 20 mM Tris-HCl (pH 7.5), 2 mM EGTA, 25 mM β-glycerophosphate, 2 mM DTT, 1 mM vanadate, 1 mM PMSF (phenylmethylsulfonyl fluoride) and 1% aprotinin, wherein the buffer was used in an amount of 300 µl relative to cells obtained per µlate (diameter: 100 mm). The resultant cell homogenate was centrifuged at 1000×g for 3 minutes, followed by a further centrifugation at 400,000×g for 20 minutes, thereby obtaining a supernatant. The obtained supernatant was used as the cell extract.

To 200 µl of the cell extract was added 3 µl of an antiserum (anti-MKK7 antiserum and anti-SEK1/MKK4 antiserum were separately used), and a reaction for preparing an immune complex was allowed to proceed while incubating at 4° C. for 1 hour. Subsequently, 30 μl of a slurry (solid content: 50%) of Protein A Sepharose Beads (manufactured and sold by Pharmacia Biotech AB, Sweden) was added to the mixture, followed by further incubation at 4° C. for 1 hour, to thereby adsorb the immune complex to the beads. The beads were washed three times with a solution containing 20 mM Tris-HCl (pH 7.5), 500 mM NaCl, 2 mM DTT and 0.05% Tween 20. Then, the immune complex adsorbed on the beads was incubated with 1 μg of His-SAPK and 3 μg of GST-cJun (the 1st to 79th amino acid residues of whole Jun) in a final volume of 15 μl of a reaction buffer containing 20 mM Tris-HCl (pH 7.5), 20 MM $MgCl_2$, and 100 μM [γ-$^{32}$P] ATP (3 μCi) at 30° C. for 20 minutes, to thereby conduct a reaction among the immune complex (MKK7 or SEK1/MKK4), His-SAPK and GST-cJun. After the incubation, the reaction mixture was resolved on SDS-PAGE. The phosphorylation of c-Jun was detected by autoradiography and used as an index for the activation of MKK7 or SEK1/MKK4 by TNF-α. The results are shown in FIG. 4.

As apparent from FIG. 4, TNF-α activated mouse MKK7, but did not activate mouse SEK1/MKK4.

The anti-MKK7 antiserum and anti-SEK1/MKK4 antiserum used above were prepared using His-MKK7 (prepared in Example 5) and His-XMEK2 (SEK1/MKK4 homologue of Xenopus), respectively. Rabbits were immunized with the above-mentioned protein as an antigen, and 1 mg of the protein was used per immunization. Second immunization was performed 4 weeks after the first immunization, and thereafter, subsequent immunizations were performed every three weeks. The antibody titers of the ultimate antisera were evaluated by ELISA, and each antiserum in 100,000-fold dilution was capable of reacting with the antigen.

EXAMPLE 7
Inhibition of TNF-α-induced SAPK Activation by the Dominant Negative Form of MKK7

KB cells were cotransfected with the vector pSRα-HA-SAPKα (0.5 μg) and either the vector pSRα or the vector pSRα-MKK7KL (1.5 μg) using Lipofectamine (manufactured and sold under the brand of GIBCO BRL, USA). Twenty-four hours after the transfection, TNF-α (100 ng/ml), sorbitol (0.5 M) and anisomycin (100 μg/ml) were individually used to stimulate the transfected cells for 15 minutes. Next, the cell extracts of the stimulated cells were individually prepared as follows. The cells were suspended in 0.7 M NaCl solution and washed once with ice-cold HEPES-buffered saline. Subsequently, the washed cells were homogenized in a buffer containing 20 mM Tris-HCl (pH 7.5), 2 mM EGTA, 25 mM β-glycerophosphate, 2 mM DTT, 1 mM vanadate, 1 mM PMSF and 1% aprotinin, wherein the buffer was used in an amount of 300 μl relative to cells obtained per plate (diameter: 100 mm). The resultant cell homogenate was centrifuged at 1000×g for 3 minutes, followed by a further centrifugation at 400,000×g for 20 minutes, thereby obtaining a supernatant. The obtained supernatant was used as the cell extract.

Each of the cell extracts was individually immunoprecipitated with anti-HA antibody (anti-hemagglutinin antibody) (12CA5), and the kinase activity of HA-SAPK in the immunoprecipitate was determined. The results are shown in FIG. 5.

Figure 5:
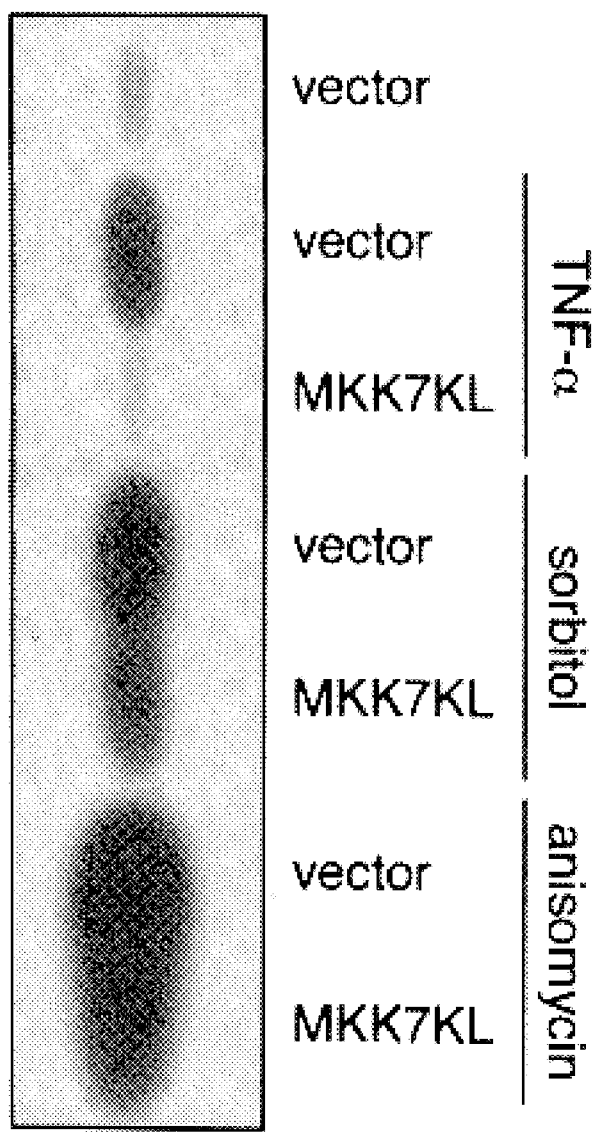
FIG. 5 is the result of the electrophoresis performed in Example 7, which shows that the expression of MKK7KL, which is a dominant negative form of mouse MKK7, suppresses the activation of SAPK/JNK.

As shown in FIG. 5, only the TNF-α-induced activation of SAPK/JNK was-suppressed in a cell expressing the dominant negative form of MKK7 (MKK7KL). From this result, it was concluded that the activation of SAPK/JNK by TNF-α is mediated by MKK7, but the activation of SAPK/JNK induced by the stimulation with sorbitol or anisomycin is mediated by a MAPK kinase different from MKK7.

EXAMPLE 8
Activation of MKK7 by a Stimulation of Fas Antigen

Jurkat cells were stimulated with 250 ng/ml anti-Fas antibody (CH-11) {manufactured and sold by Medical & Biological Laboratories, Co., Ltd. (MBL), Japan}. The cells were sampled 1, 2, 3, 4, 5 and 6 hours after the start of the stimulation, to thereby prepare cell extracts. The cell extracts were prepared as follows. The sampled cells were suspended in 0.7 M NaCl solution and washed once with ice-cold HEPES-buffered saline. Subsequently, the washed cells were homogenized in a buffer containing 20 mM Tris-HCl (pH 7.5), 2 mM EGTA, 25 mM β-glycerophosphate, 2 mM DTT, 1 mM vanadate, 1 mM PMSF and 1% aprotinin, wherein the buffer was used in an amount of 300 μl relative to cells obtained per plate (diameter: 100 mm). The resultant cell homogenate was centrifuged at 1000×g for 3 minutes, followed by a further centrifugation at 400,000×g for 20 minutes, thereby obtaining a supernatant. The obtained supernatant was used as the cell extract.

To 200 μl of the cell extract was added 3 μl of an antibody/antiserum (anti-SAPK antibody and anti-MKK7 antiserum were separately used), and a reaction for preparing an immune complex was allowed to proceed while incubating at 4° C. for 1 hour. As the anti-SAPK antibody, JNK1 antibody (rabbit polyclonal antibody) manufactured and sold by Santa Cruz Biotechnology, Inc., USA, was used. After the incubation, 30 μl of a slurry (solid content: 50%) of Protein A Sepharose Beads (manufactured and sold by Pharmacia Fine Chemicals AB, Sweden) was added to the mixture, followed by further incubation at 4° C. for 1 hour, to thereby adsorb the immune complex on the beads. The beads were washed three times with a solution containing 20 mM Tris-HCl (pH 7.5), 500 mM NaCl, 2 mM DTT and 0.05% Tween 20. With respect to the immune complex of anti-SAPK antidody, the immune complex adsorbed on the beads was incubated with 3 μg of His-Jun in a final volume of 15 μl of a reaction buffer containing 20 mM Tris-HCl (pH 7.5), 10 mM $MgCl_2$, and 100 μM [γ-$^{32}$P] ATP (3 μCi) at 30° C. for 30 minutes, to thereby conduct a reaction between the immune complex (SAPK/JNK) and His-Jun.

With respect to the immune complex of anti-MKK7 antiserum, the reaction was performed in the above-mentioned reaction buffer using GST-KN-SAPK as a substrate, and the activity of the immune complex (MKK7) was determined using the phosphorylation of SAPK as an index. GST-KN-SAPK is a fusion protein of a dominant negative form of SAPK (KN-SAPK) and GST. KN-SAPK is a variant polypeptide obtained by substituting the lysine residue in the kinase subdomain II of SAPK with a methionine residue, and the variant polypeptide is prepared by Kunkel method.

Figure 6:
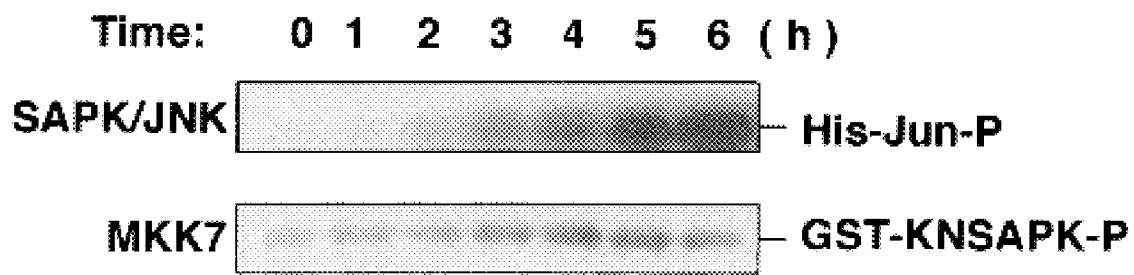
FIG. 6 is the result of the electrophoresis performed in Example 8, which shows that both mouse SAPK/JNK and MKK7 are activated by a stimulation of Fas antigen.

The results are shown in FIG. 6. Both SAPK/JNK and MKK7 were activated in a similar time course in response to a stimulation of Fas antigen. From these results, it is concluded that the activation of SAPK/JNK which was induced by the stimulation of Fas antigen was mediated by MKK7.

EXAMPLE 9
Screening for an Inhibitor of MKK7 of the Present Invention by Using MKK7

In order to screen an inhibitor of MKK7, a completely activated MKK7 was prepared as follows. Illustratively stated, as an activation factor for MKK7, MEKK1 which is suspected to exist in the upstream of MKK7 and activate MKK7, was used. A commercially available MEKK1 gene (manufactured and sold by Stratagene Cloning Systems, USA) was inserted into an *E. coli* expression vector in which the origin of replication (ori) is p15A, to thereby prepare recombinant MEKK1 vector. The whole DNA of human MKK7 was inserted into vector pGEX-4T1 (manufactured and sold by Pharmacia Biotech AB, Sweden), to thereby prepare recombinant GST-MKK7 vector. Two recombinant expression vectors prepared above were co-transformed into *E. coli* DH5α to thereby obtain an activated GST-MKK7, and the activated GST-MKK7 was purified from *E. coli* using Glutathione-Sepharose 4B column (manufactured and sold by Pharmacia Biotech AB, Sweden).

A gene encoding human JNK1 was inserted into vector pGEX-4T1, thereby preparing recombinant GST-JNK1 vector, and the prepared recombinant vector was transformed into and expressed in *E. coli*. GST-JNK1 was purified from the transformants using Glutathione-Sepharose 4B column (manufactured and sold by Pharmacia Biotech AB, Sweden). The purified JNK1 was used as a substrate for MKK7.

Figure 7:
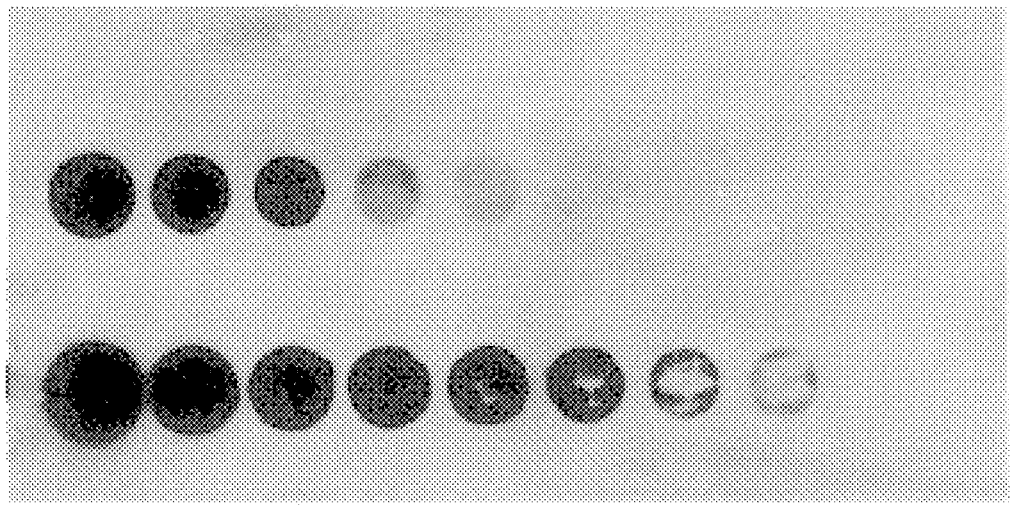
FIG. 7 is the result of the dot hybridization performed in Example 9, which shows that activated MKK7 phosphorylates JNK1, and that the density of the dots representing the phosphorylated JNK1 increases in accordance with the increase in the concentration of activated MKK7.

Using the activated MKK7 and JNK1 obtained above, the activity of MKK7 was determined in the following manner. A reaction system was prepared so that the final volume of 50 μl contains 0.1 μM MKK7, 0.2 μM JNK1, 50 mM Tris-HCl (pH 7.5), 0.1 mM EGTA, 0.1% β-mercaptoethanol, 10 mM magnesium acetate, and 0.1 mM ATP. The reaction was allowed to proceed at 30° C. for 2 hours, and then, the reaction mixture was transferred to a PVDF membrane. Dot hybridization was performed using anti-activated JNK antibody (manufactured and sold by Promega Corporation, USA) to thereby detect the activated JNK1 in the reaction mixture. Results are shown in FIG. 7. As apparent from FIG. 7, the activity of MKK7 was confirmed by the presence of activated JNK1.

Using the above-mentioned method for determining the activity of MKK7, purification and identification of a substance capable of inhibiting the activity of MKK7 can be performed with ease. Illustratively stated, a sample substance, such as a culture supernatant of various microorganisms or cultured cells, or a substance selected from a compound bank, can be added to the above-mentioned reaction system used for determining the MKK7 activity. Presence of a substance capable of inhibiting the activity of MKK7 can be confirmed by dot hybridization in which a significant decrease in the density of the dots, as compared to those of the reaction system without the addition of the sample substance, indicates the presence of an inhibitory substance. Such a method can be used for screening an inhibitor of MKK7.

INDUSTRIAL APPLICABILITY

By the use of the novel MAPK kinase and the DNA coding for the same of the present invention, it has become possible to screen a novel substance having the capability to treat or prevent diseases resulting from an excess activation or inhibition of a MAP kinase cascade, and also to provide a diagnostic reagent for such diseases. Further, the DNA of the present invention encoding the MAPK kinase can be used as a gene source for gene therapy.

What is claimed is:

1. A substantially pure human mitogen-activated protein kinase (MAPK) kinase, wherein said MAPK kinase has the following characteristics:

(a) said MAPK kinase is activated by a stimulus induced by TNF-α and/or by a stimulation of Fas antigen;

(b) said MAPK kinase activates SAPK/JNK; and (c) said MAPK kinase does not activate p38; and (d) said MAPK kinase conserves fifteen amino acid residues which correspond to the following fifteen amino acid residues of SEQ ID NO:2: the 143$^{rd}$ Gly, the 145$^{th}$ Gly, the 150$^{th}$ Val, the 165$^{th}$ Lys, the 175$^{th}$ Glu, the 259$^{th}$ Asp, the 261$^{st}$ Lys, the 264$^{th}$ Asn, the 277$^{th}$ Asp, the 279$^{th}$ Gly, the 302$^{nd}$ Pro, the 303$^{rd}$ Glu, the 320$^{th}$ Asp, the 325$^{th}$ Gly and the 384$^{th}$ Arg.

2. The MAPK kinase according to claim 1, which has the amino acid sequence of SEQ ID NO: 2.

3. An isolated DNA coding for the human MAPK kinase having the following characteristics:

(a) said MAPK kinase is activated by a stimulus induced by TNF-α and/or by a stimulation of Fas antigen;

(b) said MAPK kinase activates SAPK/JNK;

(c) said MAPK kinase does not activate p38; and (d) said MAPK kinase conserves fifteen amino acid residues which correspond to the following fifteen amino acid residues of SEQ ID NO:2: the 143rd Gly, the 145$^{th}$ Gly, the 150$^{th}$ Val, the 165$^{th}$ Lys, the 175$^{th}$ Glu, the 259$^{th}$ Asp, the 261$^{st}$ Lys, the 264$^{th}$ Asn, the 277$^{th}$ Asp, the 279$^{th}$ Gly, the 302$^{nd}$ Pro, the 303$^{rd}$ Glu, the 320$^{th}$ Asp, the 325$^{th}$ Gly and the 384$^{th}$ Arg.

4. The DNA according to claim 3, which has a nucleotide sequence of SEQ ID NO: 1; or has a nucleotide sequence which is capable of hybridization with a DNA having said nucleotide sequence, wherein the hybridization conditions comprise hybridization in the presence of 1.0×SSC and 0.1% SDS at 55° C. and washing thrice in 2×SSC and 0.5% SDS at room temperature for 15 minutes, 0.1×SSC and 0.5% SDS at 37° C. for thirty minutes, and 0.1×SSC and 0.5% SDS at 68° C. for 30 minutes in this order.

5. A replica recombinant DNA which comprises a replicable expression vector and, operably inserted therein, the DNA of claim 3.

6. A cell of a microorganism or cell culture, which is transformed with the replicable recombinant DNA of claim 5.

7. The MAPK kinase according to claim 1 or 2, which is in an activated form, wherein a serine residue and/or a threonine residue in said MAPK kinase, which contribute/contributes to activation of said MAPK kinase upon being phosphorylated, are/is phosphorylated.

* * * * *

SEQUENCE LISTING

```
<160> NUMBER OF SEQ ID NOS:  20

<210> SEQ ID NO 1
<211> LENGTH: 1308
<212> TYPE: DNA
<213> ORGANISM: Homo sapiens
<220> FEATURE:
<221> NAME/KEY: CDS
<222> LOCATION: (1)..(1305)

<400> SEQUENCE: 1 atg gcg gcg tcc tcc ctg gaa cag aag ctg tcc cgc ctg gaa gca aag      48
Met Ala Ala Ser Ser Leu Glu Gln Lys Leu Ser Arg Leu Glu Ala Lys
  1               5                  10                  15 ctg aag cag gag aac cgg gag gcc cgg cgg agg atc gac ctc aac ctg      96
Leu Lys Gln Glu Asn Arg Glu Ala Arg Arg Arg Ile Asp Leu Asn Leu
             20                  25                  30 gat atc agc ccc cag cgg ccc agg ccc att att gtg atc act cta agc     144
Asp Ile Ser Pro Gln Arg Pro Arg Pro Ile Ile Val Ile Thr Leu Ser
         35                  40                  45 cct gct cct gcc ccg tcc caa cga gca gcc ctg cag ctc ccg ctg gcc     192
Pro Ala Pro Ala Pro Ser Gln Arg Ala Ala Leu Gln Leu Pro Leu Ala
     50                  55                  60 aac gat ggg ggc agc cgc tcg cca tcc tca gag agc tcc ccg cag cac     240
Asn Asp Gly Gly Ser Arg Ser Pro Ser Ser Glu Ser Ser Pro Gln His
 65                  70                  75                  80 ccc acg ccc ccc gcc cgg ccc cgc cac atg ctg ggg ctc ccg tca acc     288
Pro Thr Pro Pro Ala Arg Pro Arg His Met Leu Gly Leu Pro Ser Thr
                 85                  90                  95
```

```
ctg ttc aca ccc cgc agc atg gag agc att gag att gac cag aag ctg      336
Leu Phe Thr Pro Arg Ser Met Glu Ser Ile Glu Ile Asp Gln Lys Leu
            100                 105                 110 cag gag atc atg aag cag acg ggc tac ctg acc atc ggg ggc cag cgc      384
Gln Glu Ile Met Lys Gln Thr Gly Tyr Leu Thr Ile Gly Gly Gln Arg
        115                 120                 125 tac cag gca gaa atc aac gac ctg gag aac ttg ggc gag atg ggc agc      432
Tyr Gln Ala Glu Ile Asn Asp Leu Glu Asn Leu Gly Glu Met Gly Ser
130                 135                 140 ggc acc tgc ggc cag gtg tgg aag atg cgc ttc cgg aag acc ggc cac      480
Gly Thr Cys Gly Gln Val Trp Lys Met Arg Phe Arg Lys Thr Gly His
145                 150                 155                 160 gtc att gcc gtt aag caa atg cgg cgc tcc ggg aac aag gag gag aac      528
Val Ile Ala Val Lys Gln Met Arg Arg Ser Gly Asn Lys Glu Glu Asn
                165                 170                 175 aag cgc atc ctc atg gac ctg gat gtg gtg ctg aag agc cac gac tgc      576
Lys Arg Ile Leu Met Asp Leu Asp Val Val Leu Lys Ser His Asp Cys
            180                 185                 190 ccc tac atc gtg cag tgc ttt ggg acg ttc atc acc aac acg gac gtc      624
Pro Tyr Ile Val Gln Cys Phe Gly Thr Phe Ile Thr Asn Thr Asp Val
        195                 200                 205 ttc atc gcc atg gag ctc atg ggc acc tgc gct gag aag ctc aag aag      672
Phe Ile Ala Met Glu Leu Met Gly Thr Cys Ala Glu Lys Leu Lys Lys
    210                 215                 220 cgg atg cag ggc ccc atc ccc gag cgc att ctg ggc aag atg aca gtg      720
Arg Met Gln Gly Pro Ile Pro Glu Arg Ile Leu Gly Lys Met Thr Val
225                 230                 235                 240 gcg att gtg aag gcg ctg tac tac ctg aag gag aag cac ggt gtc atc      768
Ala Ile Val Lys Ala Leu Tyr Tyr Leu Lys Glu Lys His Gly Val Ile
                245                 250                 255 cac cgc gac gtc aag ccc tcc aac atc ctg ctg gac gag cgg ggc cag      816
His Arg Asp Val Lys Pro Ser Asn Ile Leu Leu Asp Glu Arg Gly Gln
            260                 265                 270 atc aag ctc tgc gac ttc ggc atc agc ggc cgc ctg gtg gac tcc aaa      864
Ile Lys Leu Cys Asp Phe Gly Ile Ser Gly Arg Leu Val Asp Ser Lys
        275                 280                 285 gcc aag acg cgg agc gcc ggc tgt gcc gcc tac atg gca ccc gag cgc      912
Ala Lys Thr Arg Ser Ala Gly Cys Ala Ala Tyr Met Ala Pro Glu Arg
    290                 295                 300 att gac ccc cca gac ccc acc aag ccg gac tat gac atc cgg gcc gac      960
Ile Asp Pro Pro Asp Pro Thr Lys Pro Asp Tyr Asp Ile Arg Ala Asp
305                 310                 315                 320 gta tgg agc ctg ggc atc tcg ttg gtg gag ctg gca aca gga cag ttt     1008
Val Trp Ser Leu Gly Ile Ser Leu Val Glu Leu Ala Thr Gly Gln Phe
                325                 330                 335 ccc tac aag aac tgc aag acg gac ttt gag gtc ctt acc aaa gtc cta     1056
Pro Tyr Lys Asn Cys Lys Thr Asp Phe Glu Val Leu Thr Lys Val Leu
            340                 345                 350 cag gaa gag ccc ccg ctt ctg ccc gga cac atg ggc ttc tcg ggg gac     1104
Gln Glu Glu Pro Pro Leu Leu Pro Gly His Met Gly Phe Ser Gly Asp
        355                 360                 365 ttc cag tcc ttc gtc aaa gac tgc ctt act aaa gat cac agg aag aga     1152
Phe Gln Ser Phe Val Lys Asp Cys Leu Thr Lys Asp His Arg Lys Arg
    370                 375                 380 cca aag tat aat aag cta ctt gaa cac agc ttc atc aag cgc tac gag     1200
Pro Lys Tyr Asn Lys Leu Leu Glu His Ser Phe Ile Lys Arg Tyr Glu
385                 390                 395                 400 acg ctg gag gtg gac gtg gcg tcc tgg ttc aag gat gtc atg gcg aag     1248
Thr Leu Glu Val Asp Val Ala Ser Trp Phe Lys Asp Val Met Ala Lys
```

```
                       405                 410                 415
act gag tca ccg cgg act agc ggc gtc ctg agc cag ccc cac ctg ccc      1296
Thr Glu Ser Pro Arg Thr Ser Gly Val Leu Ser Gln Pro His Leu Pro
        420                 425                 430 ttc ttc agg tag                                                      1308
Phe Phe Arg
        435

<210> SEQ ID NO 2
<211> LENGTH: 435
<212> TYPE: PRT
<213> ORGANISM: Homo sapiens

<400> SEQUENCE: 2

Met Ala Ala Ser Ser Leu Glu Gln Lys Leu Ser Arg Leu Glu Ala Lys
  1               5                  10                  15

Leu Lys Gln Glu Asn Arg Glu Ala Arg Arg Ile Asp Leu Asn Leu
                 20                  25                  30

Asp Ile Ser Pro Gln Arg Pro Arg Pro Ile Ile Val Ile Thr Leu Ser
             35                  40                  45

Pro Ala Pro Ala Pro Ser Gln Arg Ala Ala Leu Gln Leu Pro Leu Ala
 50                  55                  60

Asn Asp Gly Gly Ser Arg Ser Pro Ser Ser Glu Ser Ser Pro Gln His
 65                  70                  75                  80

Pro Thr Pro Pro Ala Arg Pro Arg His Met Leu Gly Leu Pro Ser Thr
                 85                  90                  95

Leu Phe Thr Pro Arg Ser Met Glu Ser Ile Glu Ile Asp Gln Lys Leu
                100                 105                 110

Gln Glu Ile Met Lys Gln Thr Gly Tyr Leu Thr Ile Gly Gly Gln Arg
            115                 120                 125

Tyr Gln Ala Glu Ile Asn Asp Leu Glu Asn Leu Gly Glu Met Gly Ser
        130                 135                 140

Gly Thr Cys Gly Gln Val Trp Lys Met Arg Phe Arg Lys Thr Gly His
145                 150                 155                 160

Val Ile Ala Val Lys Gln Met Arg Arg Ser Gly Asn Lys Glu Glu Asn
                165                 170                 175

Lys Arg Ile Leu Met Asp Leu Asp Val Val Leu Lys Ser His Asp Cys
            180                 185                 190

Pro Tyr Ile Val Gln Cys Phe Gly Thr Phe Ile Thr Asn Thr Asp Val
        195                 200                 205

Phe Ile Ala Met Glu Leu Met Gly Thr Cys Ala Glu Lys Leu Lys Lys
    210                 215                 220

Arg Met Gln Gly Pro Ile Pro Glu Arg Ile Leu Gly Lys Met Thr Val
225                 230                 235                 240

Ala Ile Val Lys Ala Leu Tyr Tyr Leu Lys Glu Lys His Gly Val Ile
                245                 250                 255

His Arg Asp Val Lys Pro Ser Asn Ile Leu Leu Asp Glu Arg Gly Gln
            260                 265                 270

Ile Lys Leu Cys Asp Phe Gly Ile Ser Gly Arg Leu Val Asp Ser Lys
        275                 280                 285

Ala Lys Thr Arg Ser Ala Gly Cys Ala Ala Tyr Met Ala Pro Glu Arg
    290                 295                 300

Ile Asp Pro Pro Asp Pro Thr Lys Pro Asp Tyr Asp Ile Arg Ala Asp
305                 310                 315                 320

Val Trp Ser Leu Gly Ile Ser Leu Val Glu Leu Ala Thr Gly Gln Phe
```

-continued

```
                    325                 330                 335
Pro Tyr Lys Asn Cys Lys Thr Asp Phe Glu Val Leu Thr Lys Val Leu
                340                 345                 350

Gln Glu Glu Pro Pro Leu Leu Pro Gly His Met Gly Phe Ser Gly Asp
            355                 360                 365

Phe Gln Ser Phe Val Lys Asp Cys Leu Thr Lys Asp His Arg Lys Arg
        370                 375                 380

Pro Lys Tyr Asn Lys Leu Leu Glu His Ser Phe Ile Lys Arg Tyr Glu
385                 390                 395                 400

Thr Leu Glu Val Asp Val Ala Ser Trp Phe Lys Asp Val Met Ala Lys
                405                 410                 415

Thr Glu Ser Pro Arg Thr Ser Gly Val Leu Ser Gln Pro His Leu Pro
            420                 425                 430

Phe Phe Arg
        435

<210> SEQ ID NO 3
<211> LENGTH: 1518
<212> TYPE: DNA
<213> ORGANISM: Mus musculus
<220> FEATURE:
<221> NAME/KEY: CDS
<222> LOCATION: (1)..(1404)

<400> SEQUENCE: 3 atg gcg gcg tcc tcc ctg gag cag aag ctg tcc cgc ctg gaa gcc aag      48
Met Ala Ala Ser Ser Leu Glu Gln Lys Leu Ser Arg Leu Glu Ala Lys
  1               5                  10                  15 ctg aag cag gag aac cgt gag gcc cgc agg agg atc gac ctc aac ttg      96
Leu Lys Gln Glu Asn Arg Glu Ala Arg Arg Arg Ile Asp Leu Asn Leu
             20                  25                  30 gat atc agc cca cag cgg ccc agg ccc att att gtg atc act cta agc     144
Asp Ile Ser Pro Gln Arg Pro Arg Pro Ile Ile Val Ile Thr Leu Ser
         35                  40                  45 cct gct cct gcc ccg tcc cag cga gca gcc ctg caa ctc cca ctg gcc     192
Pro Ala Pro Ala Pro Ser Gln Arg Ala Ala Leu Gln Leu Pro Leu Ala
     50                  55                  60 aac gat ggg ggc agc cgc tca cca tcc tca gag agc tcc cca cag cac     240
Asn Asp Gly Gly Ser Arg Ser Pro Ser Ser Glu Ser Ser Pro Gln His
 65                  70                  75                  80 cct aca ccc ccc acc cgg ccc cgc cac atg ctg ggg ctc cca tca acc     288
Pro Thr Pro Pro Thr Arg Pro Arg His Met Leu Gly Leu Pro Ser Thr
                 85                  90                  95 ttg ttc aca ccg cgc agt atg gag agc atc gag att gac cag aag ctg     336
Leu Phe Thr Pro Arg Ser Met Glu Ser Ile Glu Ile Asp Gln Lys Leu
            100                 105                 110 cag gag atc atg aag cag aca ggg tac ctg act atc ggg ggc cag cgt     384
Gln Glu Ile Met Lys Gln Thr Gly Tyr Leu Thr Ile Gly Gly Gln Arg
        115                 120                 125 tat cag gca gaa atc aat gac ttg gag aac ttg ggt gag atg ggc agt     432
Tyr Gln Ala Glu Ile Asn Asp Leu Glu Asn Leu Gly Glu Met Gly Ser
    130                 135                 140 ggt acc tgt ggt cag gtg tgg aag atg cgg ttc cgg aag aca ggc cac     480
Gly Thr Cys Gly Gln Val Trp Lys Met Arg Phe Arg Lys Thr Gly His
145                 150                 155                 160 atc att gct gtt aag caa atg cgg cgc tct ggg aac aag gaa gag aat     528
Ile Ile Ala Val Lys Gln Met Arg Arg Ser Gly Asn Lys Glu Glu Asn
                165                 170                 175 aag cgc att ttg atg gac ctg gat gta gta ctc aag agc cat gac tgc     576
```

```
                Lys Arg Ile Leu Met Asp Leu Asp Val Val Leu Lys Ser His Asp Cys
                        180                 185                 190 cct tac atc gtt cag tgc ttt ggc acc ttc atc acc aac aca gac gtc            624
Pro Tyr Ile Val Gln Cys Phe Gly Thr Phe Ile Thr Asn Thr Asp Val
        195                 200                 205 ttt att gcc atg gag ctc atg ggc aca tgt gca gag aag ctg aag aaa            672
Phe Ile Ala Met Glu Leu Met Gly Thr Cys Ala Glu Lys Leu Lys Lys
    210                 215                 220 cga atg cag ggc ccc att cca gag cga atc ctg ggc aag atg act gtg            720
Arg Met Gln Gly Pro Ile Pro Glu Arg Ile Leu Gly Lys Met Thr Val
225                 230                 235                 240 gcg att gtg aaa gca ctg tac tat ctg aag gag aag cat ggc gtc atc            768
Ala Ile Val Lys Ala Leu Tyr Tyr Leu Lys Glu Lys His Gly Val Ile
                245                 250                 255 cat cgc gat gtc aaa ccc tcc aac atc ctg cta gat gag cgg ggc cag            816
His Arg Asp Val Lys Pro Ser Asn Ile Leu Leu Asp Glu Arg Gly Gln
            260                 265                 270 atc aag ctc tgt gac ttt ggc atc agt ggc cgc ctt gtt gac tcc aaa            864
Ile Lys Leu Cys Asp Phe Gly Ile Ser Gly Arg Leu Val Asp Ser Lys
        275                 280                 285 gcc aaa aca cgg agt gct ggc tgt gct gcc tat atg gct ccc gag cgc            912
Ala Lys Thr Arg Ser Ala Gly Cys Ala Ala Tyr Met Ala Pro Glu Arg
    290                 295                 300 atc gac cct cca gat ccc acc aag cct gac tat gac atc cga gct gat            960
Ile Asp Pro Pro Asp Pro Thr Lys Pro Asp Tyr Asp Ile Arg Ala Asp
305                 310                 315                 320 gtg tgg agc ctg ggc atc tca ctg gtg gag ctg gca aca gga cag ttc           1008
Val Trp Ser Leu Gly Ile Ser Leu Val Glu Leu Ala Thr Gly Gln Phe
                325                 330                 335 ccc tat aag aac tgc aag acg gac ttt gag gtc ctc acc aaa gtc cta           1056
Pro Tyr Lys Asn Cys Lys Thr Asp Phe Glu Val Leu Thr Lys Val Leu
            340                 345                 350 cag gaa gag ccc cca ctc ctg cct ggt cac atg ggc ttc tca ggg gac           1104
Gln Glu Glu Pro Pro Leu Leu Pro Gly His Met Gly Phe Ser Gly Asp
        355                 360                 365 ttc cag tca ttt gtc aaa gac tgc ctt act aaa gat cac agg aag aga           1152
Phe Gln Ser Phe Val Lys Asp Cys Leu Thr Lys Asp His Arg Lys Arg
    370                 375                 380 cca aag tat aat aag cta ctt gaa cac agc ttc atc aag cac tat gag           1200
Pro Lys Tyr Asn Lys Leu Leu Glu His Ser Phe Ile Lys His Tyr Glu
385                 390                 395                 400 ata ctc gag gtg gat gtc gcg tcc tgg ttt aag gat gtc atg gcg aag           1248
Ile Leu Glu Val Asp Val Ala Ser Trp Phe Lys Asp Val Met Ala Lys
                405                 410                 415 acc gag tcc cca agg act agt gga gtc ctg agt cag cac cat ctg ccc           1296
Thr Glu Ser Pro Arg Thr Ser Gly Val Leu Ser Gln His His Leu Pro
            420                 425                 430 ttc ttc agt ggg agt ctg gag gag tct ccc act tcc cca cct tct ccc           1344
Phe Phe Ser Gly Ser Leu Glu Glu Ser Pro Thr Ser Pro Pro Ser Pro
        435                 440                 445 aag tcc ttc cct ctg tca cca gcc atc cct cag gcc cag gca gag tgg           1392
Lys Ser Phe Pro Leu Ser Pro Ala Ile Pro Gln Ala Gln Ala Glu Trp
    450                 455                 460 gtc tcg ggc agg tag    ggacctggag tggcctggtc ccaccctctg acctcctcct        1447
Val Ser Gly Arg
465 caggccacca gtgttgccct cttcccttt taaaacaaaa tacccttgtt tgtaaatcct         1507 tagacgcttg a                                                              1518
```

-continued

```
<210> SEQ ID NO 4
<211> LENGTH: 468
<212> TYPE: PRT
<213> ORGANISM: Mus musculus

<400> SEQUENCE: 4

Met Ala Ala Ser Ser Leu Glu Gln Lys Leu Ser Arg Leu Glu Ala Lys
 1               5                  10                  15

Leu Lys Gln Glu Asn Arg Glu Ala Arg Arg Arg Ile Asp Leu Asn Leu
             20                  25                  30

Asp Ile Ser Pro Gln Arg Pro Arg Pro Ile Ile Val Ile Thr Leu Ser
         35                  40                  45

Pro Ala Pro Ala Pro Ser Gln Arg Ala Ala Leu Gln Leu Pro Leu Ala
     50                  55                  60

Asn Asp Gly Gly Ser Arg Ser Pro Ser Ser Glu Ser Ser Pro Gln His
 65                  70                  75                  80

Pro Thr Pro Pro Thr Arg Pro Arg His Met Leu Gly Leu Pro Ser Thr
                 85                  90                  95

Leu Phe Thr Pro Arg Ser Met Glu Ser Ile Glu Ile Asp Gln Lys Leu
            100                 105                 110

Gln Glu Ile Met Lys Gln Thr Gly Tyr Leu Thr Ile Gly Gly Gln Arg
        115                 120                 125

Tyr Gln Ala Glu Ile Asn Asp Leu Glu Asn Leu Gly Glu Met Gly Ser
    130                 135                 140

Gly Thr Cys Gly Gln Val Trp Lys Met Arg Phe Arg Lys Thr Gly His
145                 150                 155                 160

Ile Ile Ala Val Lys Gln Met Arg Arg Ser Gly Asn Lys Glu Glu Asn
                165                 170                 175

Lys Arg Ile Leu Met Asp Leu Asp Val Val Leu Lys Ser His Asp Cys
            180                 185                 190

Pro Tyr Ile Val Gln Cys Phe Gly Thr Phe Ile Thr Asn Thr Asp Val
        195                 200                 205

Phe Ile Ala Met Glu Leu Met Gly Thr Cys Ala Glu Lys Leu Lys Lys
    210                 215                 220

Arg Met Gln Gly Pro Ile Pro Glu Arg Ile Leu Gly Lys Met Thr Val
225                 230                 235                 240

Ala Ile Val Lys Ala Leu Tyr Tyr Leu Lys Glu Lys His Gly Val Ile
                245                 250                 255

His Arg Asp Val Lys Pro Ser Asn Ile Leu Leu Asp Glu Arg Gly Gln
            260                 265                 270

Ile Lys Leu Cys Asp Phe Gly Ile Ser Gly Arg Leu Val Asp Ser Lys
        275                 280                 285

Ala Lys Thr Arg Ser Ala Gly Cys Ala Ala Tyr Met Ala Pro Glu Arg
    290                 295                 300

Ile Asp Pro Pro Asp Pro Thr Lys Pro Asp Tyr Asp Ile Arg Ala Asp
305                 310                 315                 320

Val Trp Ser Leu Gly Ile Ser Leu Val Glu Leu Ala Thr Gly Gln Phe
                325                 330                 335

Pro Tyr Lys Asn Cys Lys Thr Asp Phe Glu Val Leu Thr Lys Val Leu
            340                 345                 350

Gln Glu Glu Pro Pro Leu Leu Pro Gly His Met Gly Phe Ser Gly Asp
        355                 360                 365

Phe Gln Ser Phe Val Lys Asp Cys Leu Thr Lys Asp His Arg Lys Arg
    370                 375                 380
```

```
Pro Lys Tyr Asn Lys Leu Leu Glu His Ser Phe Ile Lys His Tyr Glu
385                 390                 395                 400

Ile Leu Glu Val Asp Val Ala Ser Trp Phe Lys Asp Val Met Ala Lys
            405                 410                 415

Thr Glu Ser Pro Arg Thr Ser Gly Val Leu Ser Gln His His Leu Pro
        420                 425                 430

Phe Phe Ser Gly Ser Leu Glu Glu Ser Pro Thr Ser Pro Pro Ser Pro
            435                 440                 445

Lys Ser Phe Pro Leu Ser Pro Ala Ile Pro Gln Ala Gln Ala Glu Trp
    450                 455                 460

Val Ser Gly Arg
465

<210> SEQ ID NO 5
<211> LENGTH: 1260
<212> TYPE: DNA
<213> ORGANISM: Mus musculus
<220> FEATURE:
<221> NAME/KEY: CDS
<222> LOCATION: (1)..(1257)

<400> SEQUENCE: 5 atg gcg gcg tcc tcc ctg gag cag aag ctg tcc cgc ctg gaa gcc aag    48
Met Ala Ala Ser Ser Leu Glu Gln Lys Leu Ser Arg Leu Glu Ala Lys
 1               5                  10                  15 ctg aag cag gag aac cgt gag gcc cgc agg agg atc gac ctc aac ttg    96
Leu Lys Gln Glu Asn Arg Glu Ala Arg Arg Arg Ile Asp Leu Asn Leu
            20                  25                  30 gat atc agc cca cag cgg ccc agg ccc acc ctg caa ctc cca ctg gcc   144
Asp Ile Ser Pro Gln Arg Pro Arg Pro Thr Leu Gln Leu Pro Leu Ala
        35                  40                  45 aac gat ggg ggc agc cgc tca cca tcc tca gag agc tcc cca cag cac   192
Asn Asp Gly Gly Ser Arg Ser Pro Ser Ser Glu Ser Ser Pro Gln His
    50                  55                  60 cct aca ccc ccc acc cgg ccc cgc cac atg ctg ggg ctc cca tca acc   240
Pro Thr Pro Pro Thr Arg Pro Arg His Met Leu Gly Leu Pro Ser Thr
65                  70                  75                  80 ttg ttc aca ccg cgc agt atg gag agc atc gag att gac cag aag ctg   288
Leu Phe Thr Pro Arg Ser Met Glu Ser Ile Glu Ile Asp Gln Lys Leu
                85                  90                  95 cag gag atc atg aag cag aca ggg tac ctg act atc ggg ggc cag cgt   336
Gln Glu Ile Met Lys Gln Thr Gly Tyr Leu Thr Ile Gly Gly Gln Arg
            100                 105                 110 tat cag gca gaa atc aat gac ttg gag aac ttg ggt gag atg ggc agt   384
Tyr Gln Ala Glu Ile Asn Asp Leu Glu Asn Leu Gly Glu Met Gly Ser
        115                 120                 125 ggt acc tgt ggt cag gtg tgg aag atg cgg ttc cgg aag aca ggc cac   432
Gly Thr Cys Gly Gln Val Trp Lys Met Arg Phe Arg Lys Thr Gly His
    130                 135                 140 atc att gct gtt aag caa atg cgg cgc tct ggg aac aag gaa gag aat   480
Ile Ile Ala Val Lys Gln Met Arg Arg Ser Gly Asn Lys Glu Glu Asn
145                 150                 155                 160 aag cgc att ttg atg gac ctg gat gta gta ctc aag agc cat gac tgc   528
Lys Arg Ile Leu Met Asp Leu Asp Val Val Leu Lys Ser His Asp Cys
                165                 170                 175 cct tac atc gtt cag tgc ttt ggc acc ttc atc acc aac aca gac gtc   576
Pro Tyr Ile Val Gln Cys Phe Gly Thr Phe Ile Thr Asn Thr Asp Val
            180                 185                 190 ttt att gcc atg gag ctc atg ggc aca tgt gca gag aag ctg aag aaa   624
```

```
Phe Ile Ala Met Glu Leu Met Gly Thr Cys Ala Glu Lys Leu Lys Lys
                195                 200                 205 cga atg cag ggc ccc att cca gag cga atc ctg ggc aag atg act gtg        672
Arg Met Gln Gly Pro Ile Pro Glu Arg Ile Leu Gly Lys Met Thr Val
    210                 215                 220 gcg att gtg aaa gca ctg tac tat ctg aag gag aag cat ggc gtc atc        720
Ala Ile Val Lys Ala Leu Tyr Tyr Leu Lys Glu Lys His Gly Val Ile
225                 230                 235                 240 cat cgc gat gtc aaa ccc tcc aac atc ctg cta gat gag cgg ggc cag        768
His Arg Asp Val Lys Pro Ser Asn Ile Leu Leu Asp Glu Arg Gly Gln
                245                 250                 255 atc aag ctc tgt gac ttt ggc atc agt ggc cgc ctt gtt gac tcc aaa        816
Ile Lys Leu Cys Asp Phe Gly Ile Ser Gly Arg Leu Val Asp Ser Lys
            260                 265                 270 gcc aaa aca cgg agt gct ggc tgt gct gcc tat atg gct ccc gag cgc        864
Ala Lys Thr Arg Ser Ala Gly Cys Ala Ala Tyr Met Ala Pro Glu Arg
        275                 280                 285 atc gac cct cca gat ccc acc aag cct gac tat gac atc cga gct gat        912
Ile Asp Pro Pro Asp Pro Thr Lys Pro Asp Tyr Asp Ile Arg Ala Asp
290                 295                 300 gtg tgg agc ctg ggc atc tca ctg gtg gag ctg gca aca gga cag ttc        960
Val Trp Ser Leu Gly Ile Ser Leu Val Glu Leu Ala Thr Gly Gln Phe
305                 310                 315                 320 ccc tat aag aac tgc aag acg gac ttt gag gtc ctc acc aaa gtc cta       1008
Pro Tyr Lys Asn Cys Lys Thr Asp Phe Glu Val Leu Thr Lys Val Leu
                325                 330                 335 cag gaa gag ccc cca ctc ctg cct ggt cac atg ggc ttc tca ggg gac       1056
Gln Glu Glu Pro Pro Leu Leu Pro Gly His Met Gly Phe Ser Gly Asp
            340                 345                 350 ttc cag tca ttt gtc aaa gac tgc ctt act aaa gat cac agg aag aga       1104
Phe Gln Ser Phe Val Lys Asp Cys Leu Thr Lys Asp His Arg Lys Arg
        355                 360                 365 cca aag tat aat aag cta ctt gaa cac agc ttc atc aag cac tat gag       1152
Pro Lys Tyr Asn Lys Leu Leu Glu His Ser Phe Ile Lys His Tyr Glu
370                 375                 380 ata ctc gag gtg gat gtc gcg tcc tgg ttt aag gat gtc atg gcg aag       1200
Ile Leu Glu Val Asp Val Ala Ser Trp Phe Lys Asp Val Met Ala Lys
385                 390                 395                 400 acc gag tcc cca agg act agt gga gtc ctg agt cag cac cat ctg ccc       1248
Thr Glu Ser Pro Arg Thr Ser Gly Val Leu Ser Gln His His Leu Pro
                405                 410                 415 ttc ttc agg tag                                                        1260
Phe Phe Arg <210> SEQ ID NO 6
<211> LENGTH: 419
<212> TYPE: PRT
<213> ORGANISM: Mus musculus

<400> SEQUENCE: 6

Met Ala Ala Ser Ser Leu Glu Gln Lys Leu Ser Arg Leu Glu Ala Lys
1               5                   10                  15

Leu Lys Gln Glu Asn Arg Glu Ala Arg Arg Ile Asp Leu Asn Leu
            20                  25                  30

Asp Ile Ser Pro Gln Arg Pro Arg Pro Thr Leu Gln Leu Pro Leu Ala
        35                  40                  45

Asn Asp Gly Gly Ser Arg Ser Pro Ser Ser Glu Ser Pro Gln His
    50                  55                  60

Pro Thr Pro Pro Thr Arg Pro Arg His Met Leu Gly Leu Pro Ser Thr
```

```
                65                  70                  75                  80
Leu Phe Thr Pro Arg Ser Met Glu Ser Ile Glu Ile Asp Gln Lys Leu
                        85                  90                  95
Gln Glu Ile Met Lys Gln Thr Gly Tyr Leu Thr Ile Gly Gly Gln Arg
                100                 105                 110
Tyr Gln Ala Glu Ile Asn Asp Leu Glu Asn Leu Gly Glu Met Gly Ser
                115                 120                 125
Gly Thr Cys Gly Gln Val Trp Lys Met Arg Phe Arg Lys Thr Gly His
            130                 135                 140
Ile Ile Ala Val Lys Gln Met Arg Arg Ser Gly Asn Lys Glu Glu Asn
145                 150                 155                 160
Lys Arg Ile Leu Met Asp Leu Asp Val Val Leu Lys Ser His Asp Cys
                165                 170                 175
Pro Tyr Ile Val Gln Cys Phe Gly Thr Phe Ile Thr Asn Thr Asp Val
                180                 185                 190
Phe Ile Ala Met Glu Leu Met Gly Thr Cys Ala Glu Lys Leu Lys Lys
            195                 200                 205
Arg Met Gln Gly Pro Ile Pro Glu Arg Ile Leu Gly Lys Met Thr Val
210                 215                 220
Ala Ile Val Lys Ala Leu Tyr Tyr Leu Lys Glu Lys His Gly Val Ile
225                 230                 235                 240
His Arg Asp Val Lys Pro Ser Asn Ile Leu Leu Asp Glu Arg Gly Gln
                245                 250                 255
Ile Lys Leu Cys Asp Phe Gly Ile Ser Gly Arg Leu Val Asp Ser Lys
                260                 265                 270
Ala Lys Thr Arg Ser Ala Gly Cys Ala Ala Tyr Met Ala Pro Glu Arg
            275                 280                 285
Ile Asp Pro Pro Asp Pro Thr Lys Pro Asp Tyr Asp Ile Arg Ala Asp
290                 295                 300
Val Trp Ser Leu Gly Ile Ser Leu Val Glu Leu Ala Thr Gly Gln Phe
305                 310                 315                 320
Pro Tyr Lys Asn Cys Lys Thr Asp Phe Glu Val Leu Thr Lys Val Leu
                325                 330                 335
Gln Glu Glu Pro Pro Leu Leu Pro Gly His Met Gly Phe Ser Gly Asp
                340                 345                 350
Phe Gln Ser Phe Val Lys Asp Cys Leu Thr Lys Asp His Arg Lys Arg
            355                 360                 365
Pro Lys Tyr Asn Lys Leu Leu Glu His Ser Phe Ile Lys His Tyr Glu
            370                 375                 380
Ile Leu Glu Val Asp Val Ala Ser Trp Phe Lys Asp Val Met Ala Lys
385                 390                 395                 400
Thr Glu Ser Pro Arg Thr Ser Gly Val Leu Ser Gln His His Leu Pro
                405                 410                 415
Phe Phe Arg

<210> SEQ ID NO 7
<211> LENGTH: 477
<212> TYPE: DNA
<213> ORGANISM: Xenopus laevis
<220> FEATURE:
<221> NAME/KEY: CDS
<222> LOCATION: (3)..(476)

<400> SEQUENCE: 7 gg ggg ccc ctc ctt aga aca gaa act ttn ccg tct gga ggc aaa att          47
```

```
            Gly Pro Leu Leu Arg Thr Glu Thr Xaa Pro Ser Gly Gly Lys Ile
             1               5                  10                  15 gaa gca gga gaa cag gga ggc ccg gag aag aac gag ctg gag atc agc       95
Glu Ala Gly Glu Gln Gly Gly Pro Glu Lys Asn Glu Leu Glu Ile Ser
             20                  25                  30 cct cag cgg cca agg ccc acc tta cag ctc cct ctt gcc aat gat gga      143
Pro Gln Arg Pro Arg Pro Thr Leu Gln Leu Pro Leu Ala Asn Asp Gly
         35                  40                  45 cat tca cgt tca gat acc cct ccc cat cat cat cct caa ctg aca gtt      191
His Ser Arg Ser Asp Thr Pro Pro His His His Pro Gln Leu Thr Val
     50                  55                  60 cga cca cgg acc ttt ctg agt tta cca cag acc aac tac ctg aca cag      239
Arg Pro Arg Thr Phe Leu Ser Leu Pro Gln Thr Asn Tyr Leu Thr Gln
 65                  70                  75 cgc agt ctg gaa agc att gaa att gac cag aag ctt caa gaa att atc      287
Arg Ser Leu Glu Ser Ile Glu Ile Asp Gln Lys Leu Gln Glu Ile Ile
 80                  85                  90                  95 aag cag act ggg tat tta gtt atc gat ggg cag aag tac cca gca gac      335
Lys Gln Thr Gly Tyr Leu Val Ile Asp Gly Gln Lys Tyr Pro Ala Asp
                100                 105                 110 atc aat gac ctg gag aat ctg ggc gag att ggt agc ggg act tgc ggt      383
Ile Asn Asp Leu Glu Asn Leu Gly Glu Ile Gly Ser Gly Thr Cys Gly
             115                 120                 125 caa ctc tgg aaa atg agg ttt aag aag acc ggg cat gtc att gca gtt      431
Gln Leu Trp Lys Met Arg Phe Lys Lys Thr Gly His Val Ile Ala Val
         130                 135                 140 aag caa atg cgt cgt tct gga aac aag gag gag aac aag cga att c        477
Lys Gln Met Arg Arg Ser Gly Asn Lys Glu Glu Asn Lys Arg Ile
     145                 150                 155

<210> SEQ ID NO 8
<211> LENGTH: 158
<212> TYPE: PRT
<213> ORGANISM: Xenopus laevis

<400> SEQUENCE: 8

Gly Pro Leu Leu Arg Thr Glu Thr Xaa Pro Ser Gly Gly Lys Ile Glu
 1               5                  10                  15

Ala Gly Glu Gln Gly Gly Pro Glu Lys Asn Glu Leu Glu Ile Ser Pro
             20                  25                  30

Gln Arg Pro Arg Pro Thr Leu Gln Leu Pro Leu Ala Asn Glu Gly His
         35                  40                  45

Ser Arg Ser Asp Thr Pro Pro His His Pro Gln Leu Thr Val Arg
     50                  55                  60

Pro Arg Thr Phe Leu Ser Leu Pro Gln Thr Asn Tyr Leu Thr Gln Arg
 65                  70                  75                  80

Ser Leu Glu Ser Ile Glu Ile Asp Gln Lys Leu Gln Glu Ile Ile Lys
             85                  90                  95

Gln Thr Gly Tyr Leu Val Ile Asp Gly Gln Lys Tyr Pro Ala Asp Ile
         100                 105                 110

Asn Asp Leu Glu Asn Leu Gly Glu Ile Gly Ser Gly Thr Cys Gly Gln
     115                 120                 125

Leu Trp Lys Met Arg Phe Lys Lys Thr Gly His Val Ile Ala Val Lys
 130                 135                 140

Gln Met Arg Arg Ser Gly Asn Lys Glu Glu Asn Lys Arg Ile
145                 150                 155

<210> SEQ ID NO 9
```

```
<211> LENGTH: 1518
<212> TYPE: DNA
<213> ORGANISM: Artificial Sequence
<220> FEATURE:
<221> NAME/KEY: CDS
<222> LOCATION: (3)..(476)
<221> NAME/KEY: MUTAGEN
<222> LOCATION: (493)..(495)
<223> OTHER INFORMATION: :

<400> SEQUENCE: 9 atg gcg gcg tcc tcc ctg gag cag aag ctg tcc cgc ctg gaa gcc aag        48
Met Ala Ala Ser Ser Leu Glu Gln Lys Leu Ser Arg Leu Glu Ala Lys
 1               5                  10                  15 ctg aag cag gag aac cgt gag gcc cgc agg agg atc gac ctc aac ttg        96
Leu Lys Gln Glu Asn Arg Glu Ala Arg Arg Arg Ile Asp Leu Asn Leu
             20                  25                  30 gat atc agc cca cag cgg ccc agg ccc att att gtg atc act cta agc       144
Asp Ile Ser Pro Gln Arg Pro Arg Pro Ile Ile Val Ile Thr Leu Ser
         35                  40                  45 cct gct cct gcc ccg tcc cag cga gca gcc ctg caa ctc cca ctg gcc       192
Pro Ala Pro Ala Pro Ser Gln Arg Ala Ala Leu Gln Leu Pro Leu Ala
     50                  55                  60 aac gat ggg ggc agc cgc tca cca tcc tca gag agc tcc cca cag cac       240
Asn Asp Gly Gly Ser Arg Ser Pro Ser Ser Glu Ser Ser Pro Gln His
 65                  70                  75                  80 cct aca ccc ccc acc cgg ccc cgc cac atg ctg ggg ctc cca tca acc       288
Pro Thr Pro Pro Thr Arg Pro Arg His Met Leu Gly Leu Pro Ser Thr
                 85                  90                  95 ttg ttc aca ccg cgc agt atg gag agc atc gag att gac cag aag ctg       336
Leu Phe Thr Pro Arg Ser Met Glu Ser Ile Glu Ile Asp Gln Lys Leu
            100                 105                 110 cag gag atc atg aag cag aca ggg tac ctg act atc ggg ggc cag cgt       384
Gln Glu Ile Met Lys Gln Thr Gly Tyr Leu Thr Ile Gly Gly Gln Arg
        115                 120                 125 tat cag gca gaa atc aat gac ttg gag aac ttg ggt gag atg ggc agt       432
Tyr Gln Ala Glu Ile Asn Asp Leu Glu Asn Leu Gly Glu Met Gly Ser
    130                 135                 140 ggt acc tgt ggt cag gtg tgg aag atg cgg ttc cgg aag aca ggc cac       480
Gly Thr Cys Gly Gln Val Trp Lys Met Arg Phe Arg Lys Thr Gly His
145                 150                 155                 160 atc att gct gtt ctg cag atg cgg cgc tct ggg aac aag gaa gag aat       528
Ile Ile Ala Val Leu Gln Met Arg Arg Ser Gly Asn Lys Glu Glu Asn
                165                 170                 175 aag cgc att ttg atg gac ctg gat gta gta ctc aag agc cat gac tgc       576
Lys Arg Ile Leu Met Asp Leu Asp Val Val Leu Lys Ser His Asp Cys
            180                 185                 190 cct tac atc gtt cag tgc ttt ggc acc ttc atc acc aac aca gac gtc       624
Pro Tyr Ile Val Gln Cys Phe Gly Thr Phe Ile Thr Asn Thr Asp Val
        195                 200                 205 ttt att gcc atg gag ctc atg ggc aca tgt gca gag aag ctg aag aaa       672
Phe Ile Ala Met Glu Leu Met Gly Thr Cys Ala Glu Lys Leu Lys Lys
    210                 215                 220 cga atg cag ggc ccc att cca gag cga atc ctg ggc aag atg act gtg       720
Arg Met Gln Gly Pro Ile Pro Glu Arg Ile Leu Gly Lys Met Thr Val
225                 230                 235                 240 gcg att gtg aaa gca ctg tac tat ctg aag gag aag cat ggc gtc atc       768
Ala Ile Val Lys Ala Leu Tyr Tyr Leu Lys Glu Lys His Gly Val Ile
                245                 250                 255 cat cgc gat gtc aaa ccc tcc aac atc ctg cta gat gag cgg ggc cag       816
His Arg Asp Val Lys Pro Ser Asn Ile Leu Leu Asp Glu Arg Gly Gln
            260                 265                 270
```

-continued

```
atc aag ctc tgt gac ttt ggc atc agt ggc cgc ctt gtt gac tcc aaa      864
Ile Lys Leu Cys Asp Phe Gly Ile Ser Gly Arg Leu Val Asp Ser Lys
        275                 280                 285 gcc aaa aca cgg agt gct ggc tgt gct gcc tat atg gct ccc gag cgc      912
Ala Lys Thr Arg Ser Ala Gly Cys Ala Ala Tyr Met Ala Pro Glu Arg
    290                 295                 300 atc gac cct cca gat ccc acc aag cct gac tat gac atc cga gct gat      960
Ile Asp Pro Pro Asp Pro Thr Lys Pro Asp Tyr Asp Ile Arg Ala Asp
305                 310                 315                 320 gtg tgg agc ctg ggc atc tca ctg gtg gag ctg gca aca gga cag ttc     1008
Val Trp Ser Leu Gly Ile Ser Leu Val Glu Leu Ala Thr Gly Gln Phe
                325                 330                 335 ccc tat aag aac tgc aag acg gac ttt gag gtc ctc acc aaa gtc cta     1056
Pro Tyr Lys Asn Cys Lys Thr Asp Phe Glu Val Leu Thr Lys Val Leu
            340                 345                 350 cag gaa gag ccc cca ctc ctg cct ggt cac atg ggc ttc tca ggg gac     1104
Gln Glu Glu Pro Pro Leu Leu Pro Gly His Met Gly Phe Ser Gly Asp
        355                 360                 365 ttc cag tca ttt gtc aaa gac tgc ctt act aaa gat cac agg aag aga     1152
Phe Gln Ser Phe Val Lys Asp Cys Leu Thr Lys Asp His Arg Lys Arg
    370                 375                 380 cca aag tat aat aag cta ctt gaa cac agc ttc atc aag cac tat gag     1200
Pro Lys Tyr Asn Lys Leu Leu Glu His Ser Phe Ile Lys His Tyr Glu
385                 390                 395                 400 ata ctc gag gtg gat gtc gcg tcc tgg ttt aag gat gtc atg gcg aag     1248
Ile Leu Glu Val Asp Val Ala Ser Trp Phe Lys Asp Val Met Ala Lys
                405                 410                 415 acc gag tcc cca agg act agt gga gtc ctg agt cag cac cat ctg ccc     1296
Thr Glu Ser Pro Arg Thr Ser Gly Val Leu Ser Gln His His Leu Pro
            420                 425                 430 ttc ttc agt ggg agt ctg gag gag tct ccc act tcc cca cct tct ccc     1344
Phe Phe Ser Gly Ser Leu Glu Glu Ser Pro Thr Ser Pro Pro Ser Pro
        435                 440                 445 aag tcc ttc cct ctg tca cca gcc atc cct cag gcc cag gca gag tgg     1392
Lys Ser Phe Pro Leu Ser Pro Ala Ile Pro Gln Ala Gln Ala Glu Trp
    450                 455                 460 gtc tcg ggc agg tag      ggacctggag tggcctggtc ccaccctctg acctcctcct     1447
Val Ser Gly Arg
465 caggccacca gtgttgccct cttccctttt taaaacaaaa taccctttgtt tgtaaatcct     1507 tagacgcttg a                                                           1518

<210> SEQ ID NO 10
<211> LENGTH: 468
<212> TYPE: PRT
<213> ORGANISM:

<400> SEQUENCE: 10

Met Ala Ala Ser Ser Leu Glu Gln Lys Leu Ser Arg Leu Glu Ala Lys
 1               5                  10                  15

Leu Lys Gln Glu Asn Arg Glu Ala Arg Arg Ile Asp Leu Asn Leu
            20                  25                  30

Asp Ile Ser Pro Gln Arg Pro Arg Pro Ile Ile Val Ile Thr Leu Ser
        35                  40                  45

Pro Ala Pro Ala Pro Ser Gln Arg Ala Ala Leu Gln Leu Pro Leu Ala
    50                  55                  60

Asn Asp Gly Gly Ser Arg Ser Pro Ser Ser Glu Ser Ser Pro Gln His
65                  70                  75                  80
```

```
Pro Thr Pro Pro Thr Arg Pro Arg His Met Leu Gly Leu Pro Ser Thr
                85                  90                  95
Leu Phe Thr Pro Arg Ser Met Glu Ser Ile Glu Ile Asp Gln Lys Leu
            100                 105                 110
Gln Glu Ile Met Lys Gln Thr Gly Tyr Leu Thr Ile Gly Gly Gln Arg
        115                 120                 125
Tyr Gln Ala Glu Ile Asn Asp Leu Glu Asn Leu Gly Glu Met Gly Ser
    130                 135                 140
Gly Thr Cys Gly Gln Val Trp Lys Met Arg Phe Arg Lys Thr Gly His
145                 150                 155                 160
Ile Ile Ala Val Leu Gln Met Arg Arg Ser Gly Asn Lys Glu Glu Asn
                165                 170                 175
Lys Arg Ile Leu Met Asp Leu Asp Val Val Leu Lys Ser His Asp Cys
            180                 185                 190
Pro Tyr Ile Val Gln Cys Phe Gly Thr Phe Ile Thr Asn Thr Asp Val
        195                 200                 205
Phe Ile Ala Met Glu Leu Met Gly Thr Cys Ala Glu Lys Leu Lys Lys
    210                 215                 220
Arg Met Gln Gly Pro Ile Pro Glu Arg Ile Leu Gly Lys Met Thr Val
225                 230                 235                 240
Ala Ile Val Lys Ala Leu Tyr Tyr Leu Lys Glu Lys His Gly Val Ile
                245                 250                 255
His Arg Asp Val Lys Pro Ser Asn Ile Leu Leu Asp Glu Arg Gly Gln
            260                 265                 270
Ile Lys Leu Cys Asp Phe Gly Ile Ser Gly Arg Leu Val Asp Ser Lys
        275                 280                 285
Ala Lys Thr Arg Ser Ala Gly Cys Ala Ala Tyr Met Ala Pro Glu Arg
    290                 295                 300
Ile Asp Pro Pro Asp Pro Thr Lys Pro Asp Tyr Asp Ile Arg Ala Asp
305                 310                 315                 320
Val Trp Ser Leu Gly Ile Ser Leu Val Glu Leu Ala Thr Gly Gln Phe
                325                 330                 335
Pro Tyr Lys Asn Cys Lys Thr Asp Phe Glu Val Leu Thr Lys Val Leu
            340                 345                 350
Gln Glu Glu Pro Pro Leu Leu Pro Gly His Met Gly Phe Ser Gly Asp
        355                 360                 365
Phe Gln Ser Phe Val Lys Asp Cys Leu Thr Lys Asp His Arg Lys Arg
    370                 375                 380
Pro Lys Tyr Asn Lys Leu Leu Glu His Ser Phe Ile Lys His Tyr Glu
385                 390                 395                 400
Ile Leu Glu Val Asp Val Ala Ser Trp Phe Lys Asp Val Met Ala Lys
                405                 410                 415
Thr Glu Ser Pro Arg Thr Ser Gly Val Leu Ser Gln His His Leu Pro
            420                 425                 430
Phe Phe Ser Gly Ser Leu Glu Glu Ser Pro Thr Ser Pro Pro Ser Pro
        435                 440                 445
Lys Ser Phe Pro Leu Ser Pro Ala Ile Pro Gln Ala Gln Ala Glu Trp
    450                 455                 460
Val Ser Gly Arg
465

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial Sequence:  PCR primer
      used in 5' RACE method performed in Example 2 for amplifying the
      5' end of human MKK7

<400> SEQUENCE: 11
tttggtctct tcctgtgatc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:  PCR primer
      used in 5' RACE method performed in Example 2 for amplifying the
      5' end of human MKK7

<400> SEQUENCE: 12
tgcttaacgg caatgacgtg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:  PCR primer
      used in 5' RACE method performed in Example 2 for amplifying the
      5' end of human MKK7

<400> SEQUENCE: 13
ttgatttctg cctggtagcg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:  PCR primer
      used in 3' RACE method performed in Example 2 for amplifying the
      3' end of human MKK7

<400> SEQUENCE: 14
cagtccttcg tcaaagactg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:  PCR primer
      used in 3' RACE method performed in Example 2 for amplifying the
      3' end of human MKK7

<400> SEQUENCE: 15
cagtccttcg tcaaagactg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  5' end
      primer used in Example 2 for amplifying the sequence in between
      the 5' and 3' sequences of human MKK7

<400> SEQUENCE: 16
```

```
cgctaccagg cagaaatcaa                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:  3' end
      primer used in Example 2 for amplifying the sequence in between
      the 5' and 3' sequences of human MKK7

<400> SEQUENCE: 17
tttggtctct tcctgtgatc                                              20

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence:  Synthetic
      oligo- nucleotide used in Example 4 for preparing the dominant
      negative form of MKK7

<400> SEQUENCE: 18
cagggcacat cattgctgtt ctgcagatgc ggcgctctgg gaac                   44

<210> SEQ ID NO 19
<211> LENGTH: 56
<212> TYPE: DNA
<213> ORGANISM: Artificial Sequence
<220> FEATURE:
<223> OTHER INFORMATION: Description of Artificial Sequence:  Synthetic
      oligo- nucleotide used in Example 5 for preparing vector
      pSRalpha-HA1

<400> SEQUENCE: 19
gatcgccgcc accatgtacc catacgacgt cccagattac gctcccggga gatctg      56

<210> SEQ ID NO 20
<211> LENGTH: 56
<212> TYPE: DNA
<213> ORGANISM: Artificial Sequence
<220> FEATURE:
<223> OTHER INFORMATION: Description of Artificial Sequence:  Synthetic
      oligo- nucleotide used in Example 5 for preparing vector
      pSRalpha-HA1

<400> SEQUENCE: 20
aattcagatc tcccgggagc gtaatctggg acgtcgtatg ggtacatggt ggcggc      56
```